United States Patent
Hasty et al.

(10) Patent No.: US 7,482,323 B2
(45) Date of Patent: Jan. 27, 2009

(54) INTRACELLULAR INTERLEUKIN-1 RECEPTOR ANTAGONIST AND USES THEREOF

(75) Inventors: Karen A. Hasty, Memphis, TN (US); Arnold Postlethwaite, Eads, TN (US); Sivadasan Kanangat, Cordova, TN (US)

(73) Assignee: The University of Tennessee Research Foundation, Knoxville, TN (US)

( * ) Notice: Subject to any disclaimer, the term of this patent is extended or adjusted under 35 U.S.C. 154(b) by 138 days.

(21) Appl. No.: 11/072,170

(22) Filed: Mar. 4, 2005

(65) Prior Publication Data

US 2005/0260159 A1    Nov. 24, 2005

Related U.S. Application Data

(60) Provisional application No. 60/550,108, filed on Mar. 4, 2004.

(51) Int. Cl.
*A61K 38/00* (2006.01)
(52) U.S. Cl. .......................... 514/12; 530/300
(58) Field of Classification Search ....................... None
See application file for complete search history.

(56) References Cited

U.S. PATENT DOCUMENTS 5,747,444 A * 5/1998 Haskill et al. .................. 514/2
5,872,095 A * 2/1999 Haskill et al. .................. 514/2

OTHER PUBLICATIONS

Caron J.P., et al. Chondroprotective effect of intraarticular injections of interleukin-1 receptor antagonist in experimental osteoarthritis. Arthritis and Rheumatism. 1996. vol. 39(9), p. 1535-1544.*

* cited by examiner

*Primary Examiner*—Gary B. Nickol
*Assistant Examiner*—Bruce D. Hissong
(74) *Attorney, Agent, or Firm*—Benjamin Aaron Adler

(57) ABSTRACT

Matrix metalloproteinases are major mediators of tissue destruction in various chronic inflammatory disorders. The present invention demonstrates that over-expression of intracellular isoform of IL-1 receptor antagonist confers to recipient cells resistance to signaling pathways of proinflammatory cytokines (such as tumor necrosis factor alpha and IL-1 beta) that induce matrix metalloproteinase and subsequent tissue degradation. Hence, over-expression of intracellular IL-1 receptor antagonist may inhibit tissue destruction in various inflammatory disorders such as rheumatoid arthritis, other arthritides, degenerative intervertebral disc disease and chronic skin ulcers that occurs in diabetes mellitus and bed-ridden patients.

4 Claims, 29 Drawing Sheets

INTRACELLULAR INTERLEUKIN-1 RECEPTOR ANTAGONIST AND USES THEREOF

CROSS REFERENCE TO RELATED APPLICATION

This non-provisional application claims benefit of provisional application U.S. Ser. No. 60/550,108 filed Mar. 4, 2004, now abandoned.

FEDERAL FUNDING LEGEND

This invention was produced in part using funds obtained through grants from the U.S. Department of Veterans Affairs and the National Institutes of Health. Consequently, the federal government has certain rights in this invention.

BACKGROUND OF THE INVENTION

1. Field of the Invention

The present invention relates generally to inflammatory cytokines, matrix metalloproteinases and maintenance of extracellular matrix. More specifically, the present invention discloses uses of an intracellular interleukin-1 receptor antagonist to inhibit degradation of extracellular matrix.

2. Description of the Related Art

IL-1 is one of the most important inflammatory cytokines, which stimulate a variety of cells to release pro-inflammatory proteins that result in joint inflammation and destruction. Because of its central role in causing joint destruction, interleukin-1 is now a target for the treatment of arthritis.

IL-1 has a naturally occurring inhibitory protein called IL-1 receptor antagonist (IL-1ra). This inhibitory protein has two isoforms, a secreted isoform (sIL-1ra) and an intracellular isoform (icIL-1ra), which results from alternate splicing of RNA encoding the amino-termini. The role of the secreted isoform of IL-1 receptor antagonist in the inhibition of inflammatory effects of IL-1 is due to its ability to occupy the receptor without transducing a signal.

The ability of sIL-1ra to ameliorate the development of arthritis has been well established. However, almost nothing is known about the function or mode of action of the intracellular isoform of IL-1 receptor antagonist, especially in the regulation of inflammation and degradation of extracellular matrix. The present invention fulfills this long-standing need and desire in the art by disclosing the intracellular isoform of IL-1 receptor antagonist can inhibit extracellular matrix degradation by inhibiting collagenase production.

SUMMARY OF THE INVENTION

The present invention examines the balance between synthesis and degradation of extracellular matrix. The potential role of the intracellular isoform of IL-1 receptor antagonist was examined by over-expressing the antagonist in pig articular chondrocytes or human fibroblasts. Cells over-expressing the intracellular IL-1 receptor antagonist exhibited reduced levels of collagenase (MMP-1) in response to IL-1β or TNF-a stimulation. Collagenase is a matrix metalloproteinase that is involved in the degradation of native fibrillar collagen, the predominant protein in the human body. In order to determine the mechanism of collagenase inhibition by the intracellular antagonist of IL-1 receptor, the expressions of signaling molecules were assessed. It was found that c-jun-N-terminal kinase (JNK), activity that was increased by IL-1β stimulation, was blocked in cells over-expressing the intracellular antagonist. These data demonstrate that the intracellular isoform of IL-1 receptor antagonist plays an important role in the control of cartilage degradation.

The present invention provides a method of inhibiting tissue degradation. This method comprises contacting a cell in a tissue with an intracellular isoform of IL-1 receptor antagonist and inhibiting the expression of matrix metalloproteinase via the contact, thereby inhibiting the tisse degradation.

In another embodiment, there is provided a method of treating an individual having a chronic inflammatory disorder by over-expressing a gene encoding an intracellular isoform of IL-1 receptor antagonist in a target tissue or administering peptides of intracellular isoform of IL-1 receptor antagonist to the individual.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIG. 9A: Lanes 1&9, Normal fibroblasts+PBS; Lanes 2&8, Normal fibroblasts+IL-1β; Lanes 3&7, SSc Fibroblasts+PBS; Lanes 4&6, SSc Fibroblasts+IL-1β; Lane 5, MMP-1 cDNA; and Lane M, MW Markers. The band intensities of the PCR products were measured using a 3-D densitometric scanning device (Alpha Innotech Corporation, San Leandro, Calif., USA). The values are expressed as ratio of MMP-1 to that of the housekeeping gene β-Actin (FIG. 9B).

Poly (A)+ RNA was prepared from equal numbers of normal and SSc fibroblasts stimulated for indicated times with 250 pg/ml of IL-1 beta. The first lane contains full-length undigested probe at 1/50 dilution, which migrates at the position indicated by >. The position of the fragments protected are indicated on the right:<alpha+precursor IL-1 alpha (336 bases), <ic=icIL-1ra (160 bases0, <G=G3PDH. Band volumes for the protected fragments, normalized G3PDH, are shown below the lanes. The top gel was exposed for 20 hours and the bottom gel was exposed for 1 hour.

Figure 14A:
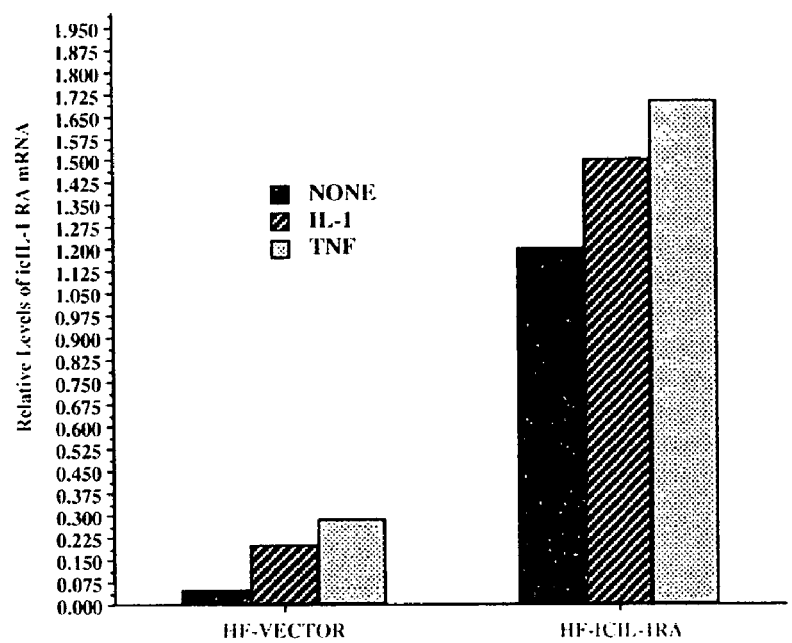
Figure 14B:
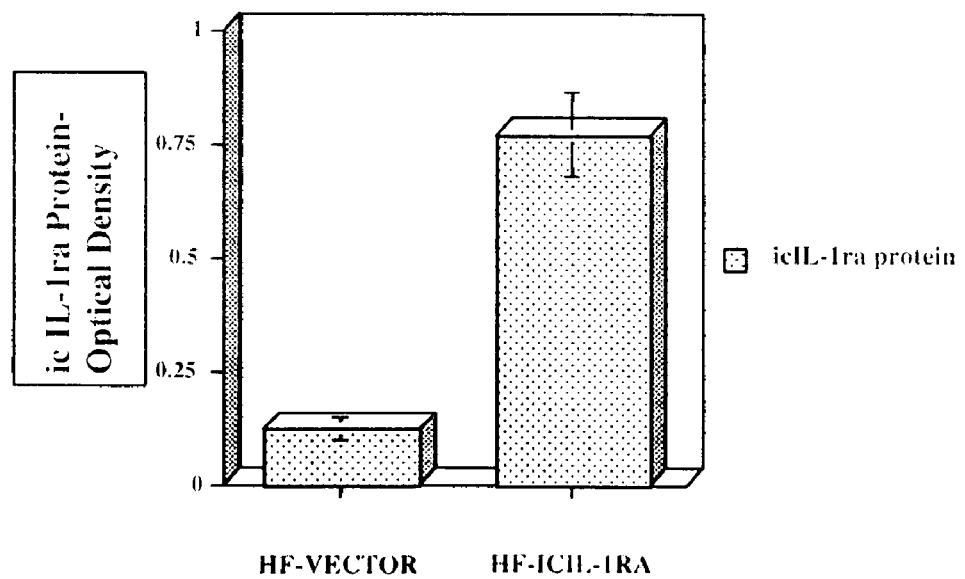

FIGS. 14A-B show over-expression of intracellular isoform of IL-1 receptor antagonist (icIL-1ra) in stably transfected fibroblasts. Equal number of cells (HF-icIL-1ra and HF-Vector) were stimulated with 1.0 ng/ml of hrIL-1b or 10 ng/ml of hrTNF-a. The cells were harvested after 24 hours, lysed in Tri-Reagent (Sigma), and total RNA was extracted and reverse transcribed. The cDNAs for icIL-1ra type1 and the housekeeping gene, GAPDH, were amplified using specific sets of primers (Table 1). The PCR products were analyzed on a 2% gel, stained with ethidium bromide and photographed. The band intensities were determined using a 3-D densitometric scanning device (Alpha Innotech Corporation, San Leandro, Calif., USA). Ratios of icIL-1ra type 1 to GAPDH messages are plotted in FIG. 14A. FIG. 14B shows equal numbers of HF-icIL-1ra and HF-Vector fibroblasts maintained in complete DMEM for 48 hours were harvested and lysed in a solution containing protease inhibitors and 50 mM Tris, 0.1% 3-{(3-cholamidopropyl)dimethylammonio}-1proanesulfonate (Sigma Aldrich Chemicals, St.Louis, Mo.), and Non-iodet P-40 pH7.5. The clarified cell lysates were tested for icIL-1ra type 1 by ELISA using reagents obtained from R&D Systems. The optical density values are plotted.

Figure 15:
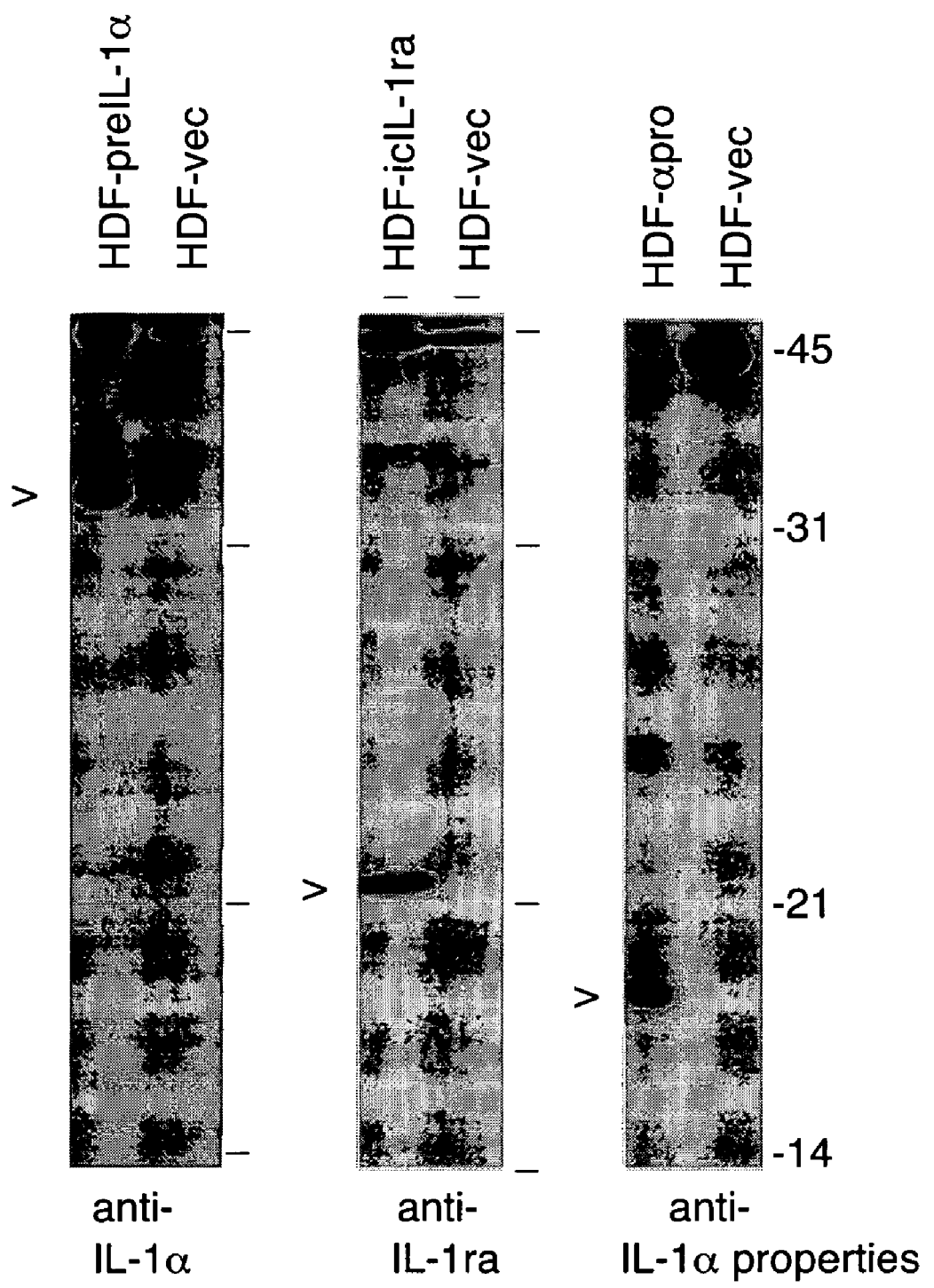

FIG. 15 shows synthesis of appropriate size protein products after transducing the normal fibroblasts with retroviral vectors expressing pre-IL-1 (HDF-preIL-1), expressing icIl-1ra (HDF-icIL-1ra), expressing propeptide region of precursor IL-1 (HDF-IL-1alpha pro) and unmodified vector (HDF-vec). A 10 cm dish of confluent, unstimulated fibroblasts of each type was incubated with methionine-free DMEM containing 2% FBS for 1 hr, followed by addition of 200 μCi/ml of $^{35}$S-methionine for 1 hr followed by lysis with detergent and immunoprecipitation of the cell extracts and SDS-PAGE analysis. Panel A: HDF-preIL-1 alpha and HDF-vec lysates immunoprecipitated with anti-IL-1 alpha. Panel B: HDF-icIL-1ra and HDF-vec lysates immunoprecipitated with anti-IL-1ra. Panel C: HDF-IL-1 alpha pro and HDF-vec lysates immunoprecipitated with rabbit antibody against recombinant IL-1 propeptide.

Figure 16:
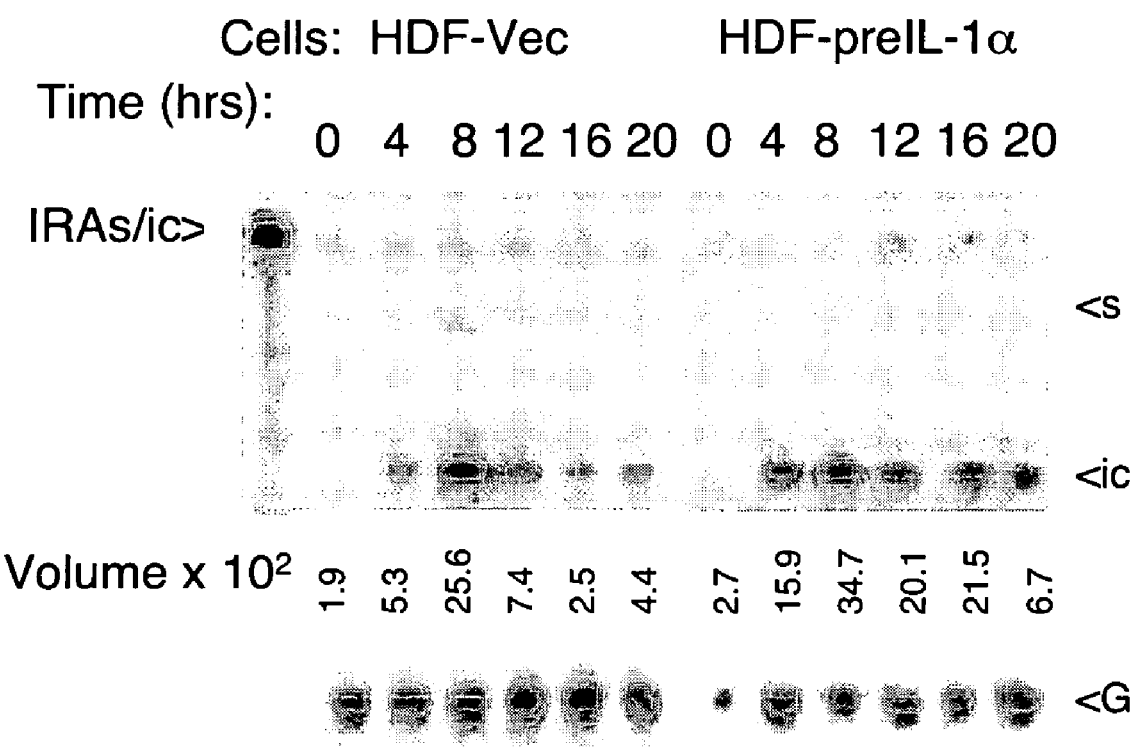

FIG. 16 shows that icIL-1ra is upregulated by preIL-1 alpha. RPA was performed on poly(A)+ prepared from HDF-vec and HDF-preIL-1 alpha stimulated for indicated times with 125 pg/ml of IL-1 beta. First lane contains full-length probe at 1/50 dilution, which migrates to the position indicated by>. The positions of the protected fragments are indicated on the right:<s=sIL-1ra, <ic=isIL-1ra, <G=G3PDH. Band volumes for fragments protected by icIL-1ra mRNA normalized to G3PDH are shown below the lanes.

Figure 17:
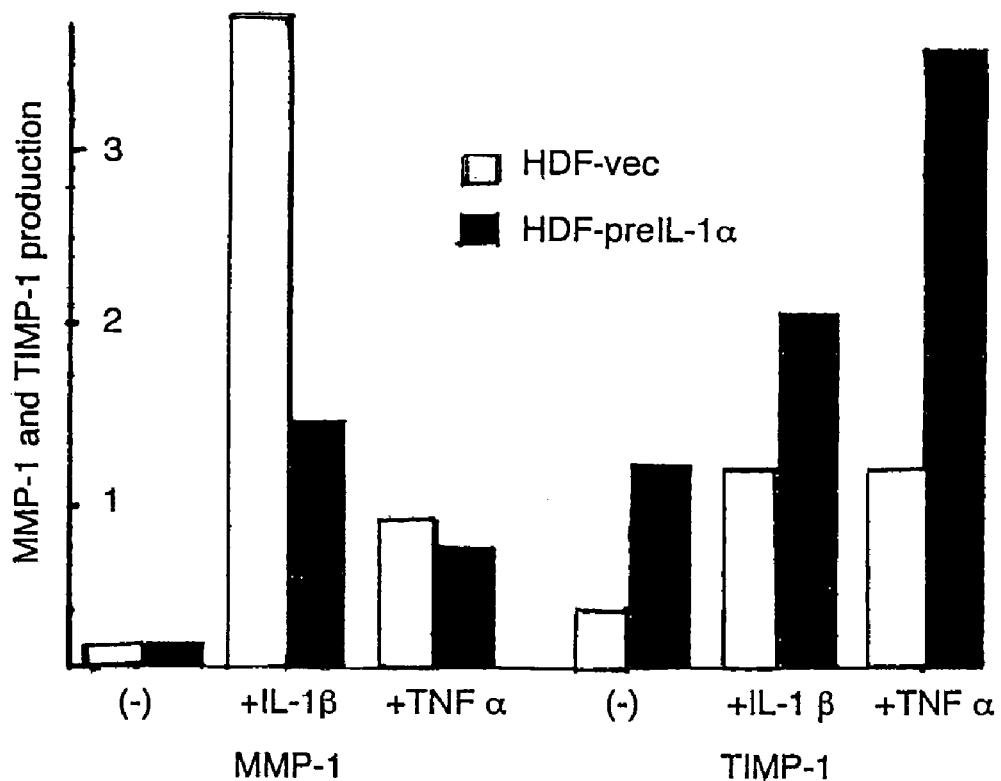

FIG. 17 shows that HDF-preIL-1 alpha have impaired MMP-1 production in response to stimulation. Confluent monolayers of fibroblasts were stimulated with 1 ng/ml hrIL-1 beta or 1 ng/ml hrTNF alpha for 72 hrs in media containing 5% FCS. The culture media was then analyzed for MMP-1 and TIMP-1 by ELISA.

Figure 18:
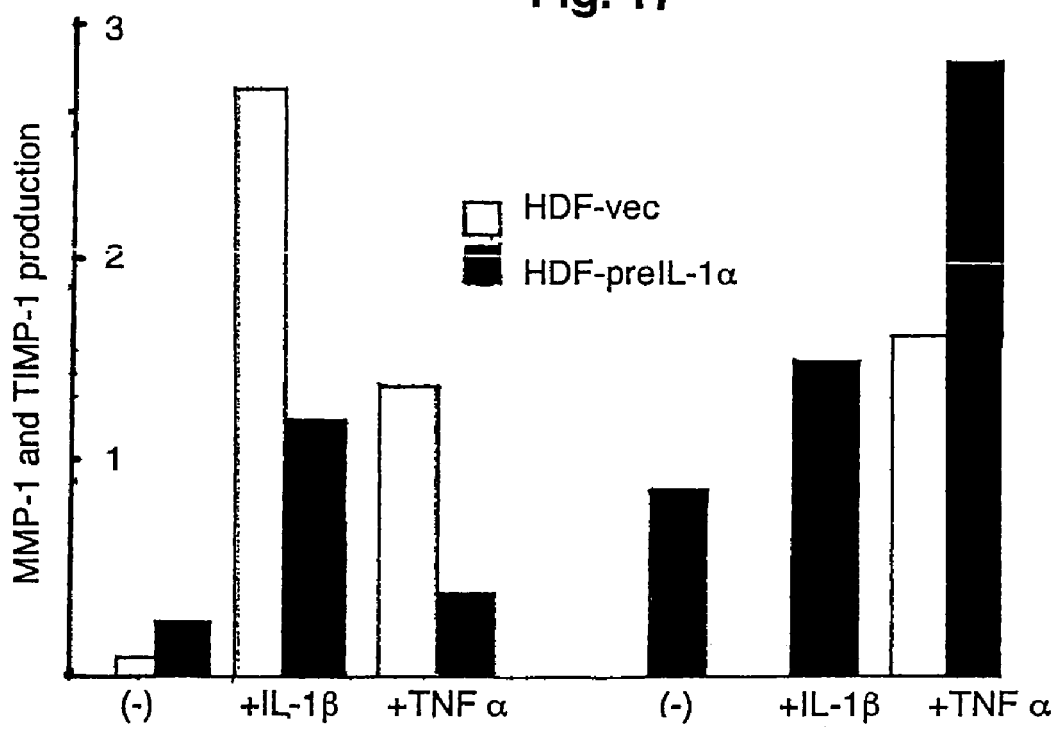

FIG. 18 shows that HDF-icIL-1ra have impaired MMP-1 production in response to stimulation. The same procedure as described above was followed and the MMP-1 and TIMP-1 production in HDF-icIL-1ra and HDF-vec was compared by ELISA.

Figure 19:
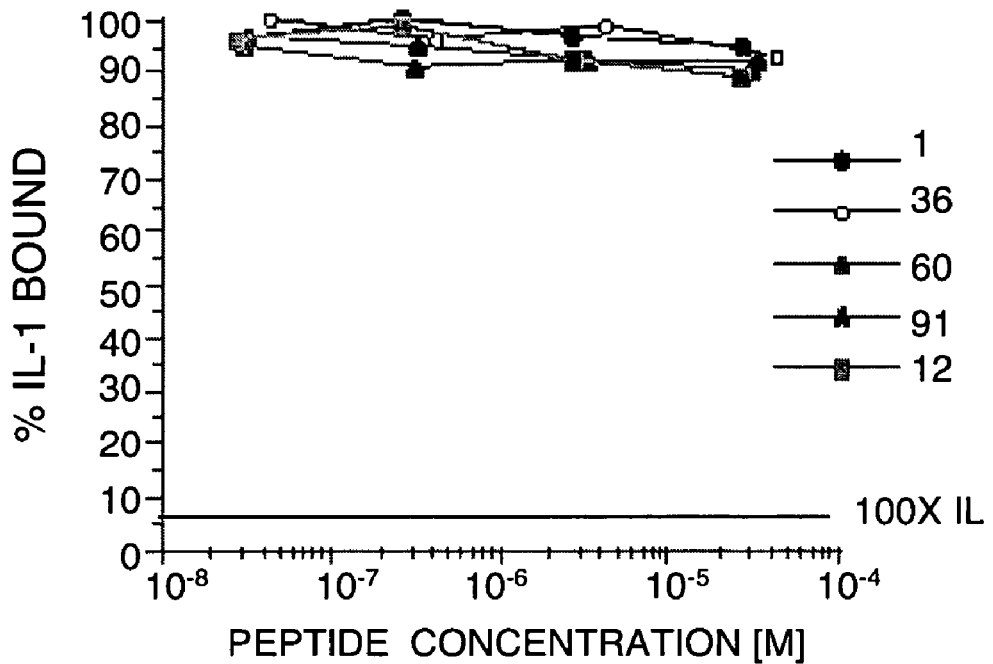

FIG. 19 shows the inability of the icIL-1ra peptides to compete with [$^{125}$I] IL-1 beta for binding to type I IL-1 receptors on murine cells. EL46.1 cells were incubated at 4° C. in presence of the sodium azide for 2 hr with and without each of the IL-1ra peptides or with soluble human recombinant interleukin 1ra (shrIL-1ra) as a control. Cells were then incubated with [$^{125}$I]hrIL-1, transferred to microfuge tubes containing phthalolate oil, centrifuged and free and bound radioactivity determined. Non-specific binding was determined in the presence of 100× excess concentration of cold hrIL-1beta.

Figure 20:
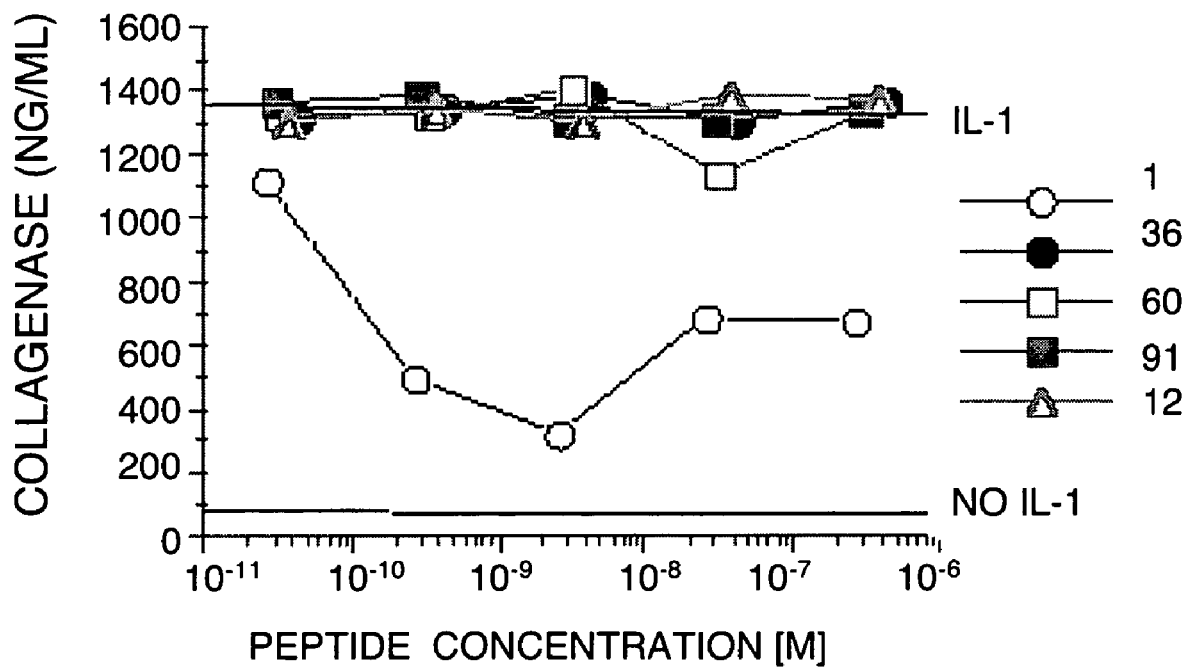

FIG. 20 shows that icIL-1ra peptide 1-35 (SEQ ID no. 13) at concentrations as low as $10^{-10}$M inhibits IL-1-induced collagenase production by fibroblasts. Confluent fibroblast cultures were preincubated for 2 hrs with or without IL-1ra peptides and then hrIL-1beta (10 pg/ml) was added to each culture. 48 hr later the supernatants were harvested and collagenase protein production was quantitated by ELISA.

Figure 21:
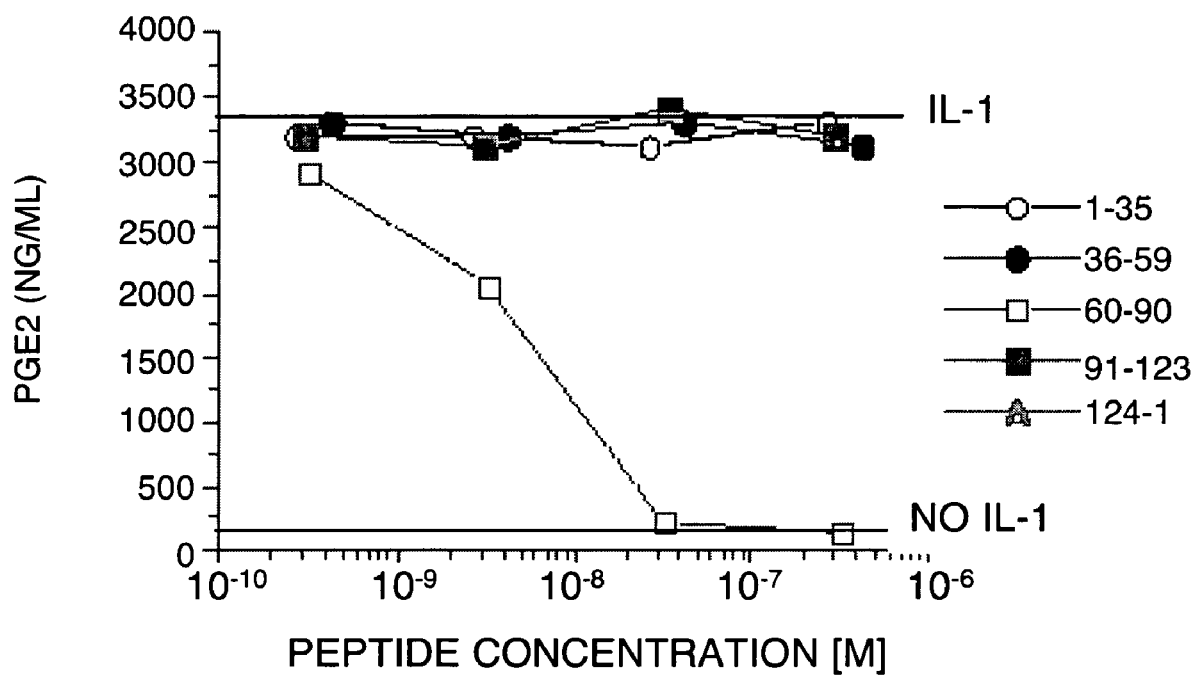

FIG. 21 shows that icIL-1ra peptide 60-90 (SEQ ID no. 15) at concentrations as low as $10^{-8}$ to $10^{-9}$ M inhibits IL-1-induced fibroblast production of prostaglandin E2 (PGE$_2$). Confluent fibroblast cultures were preincubated for 2 hrs with or without IL-1ra peptides and then hrIL-1 beta(10 pg/ml) was added to each culture. 48 hr later the supernatants were harvested and PGE$_2$ was quantitated by RIA.

Figure 22A:
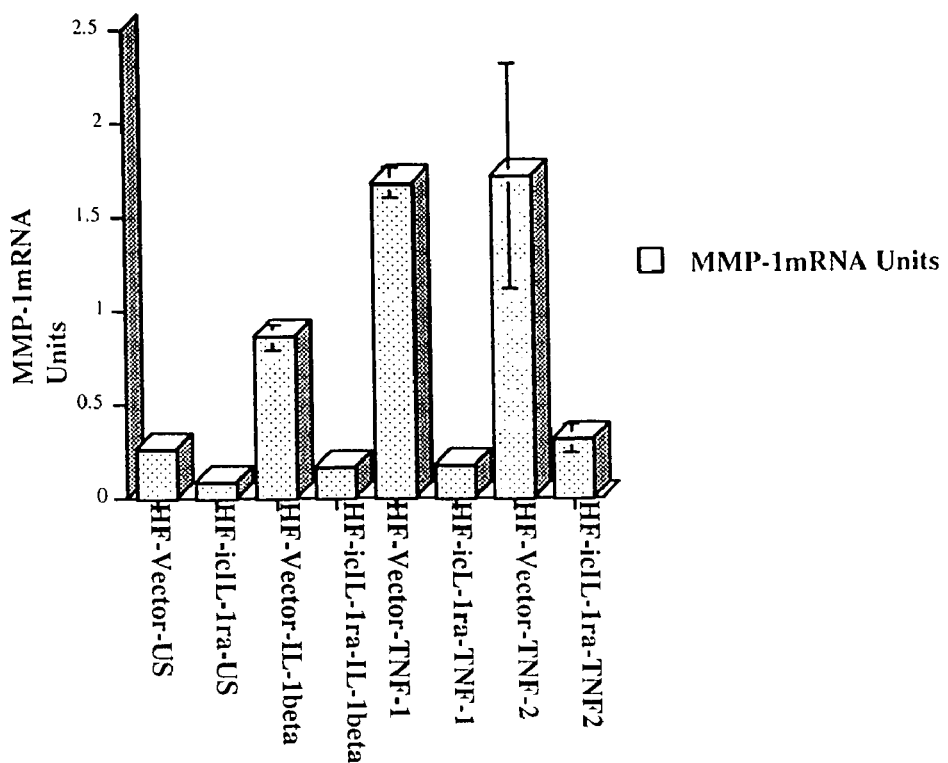
Figure 22B:
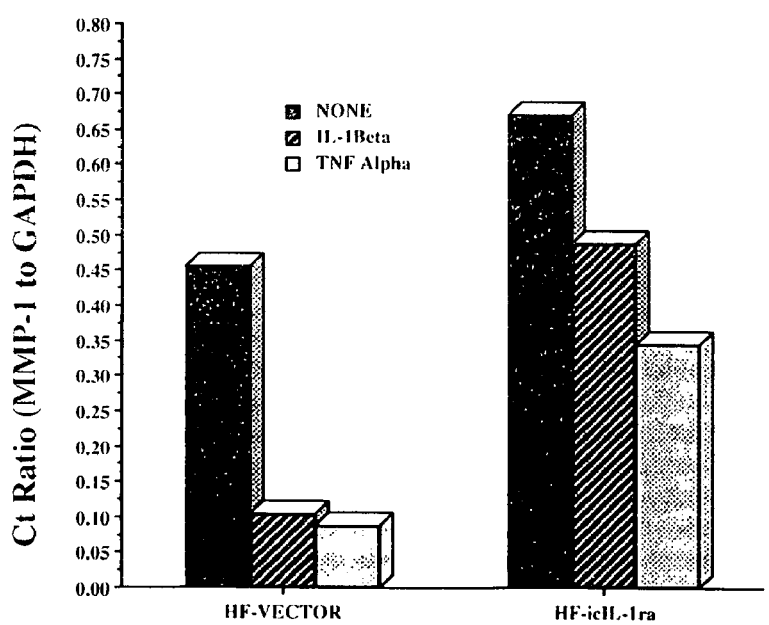
Figure 22C:
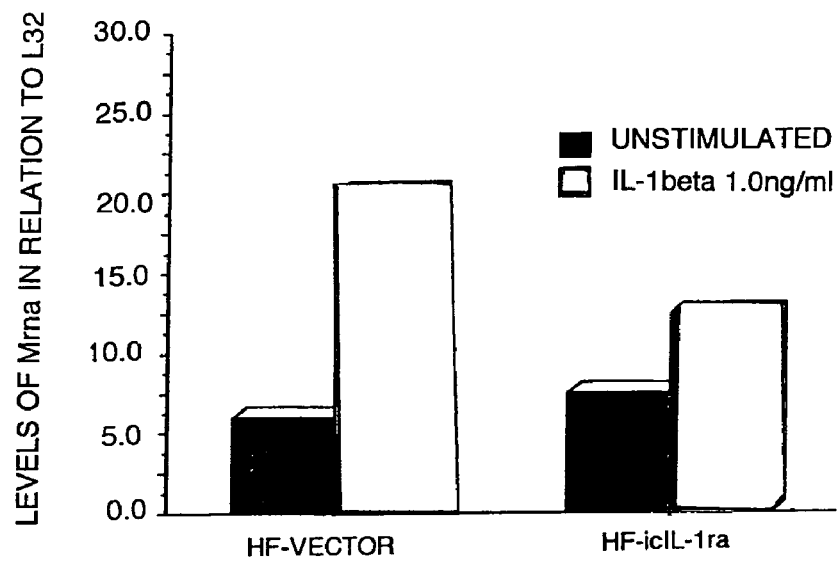
Figure 22C:
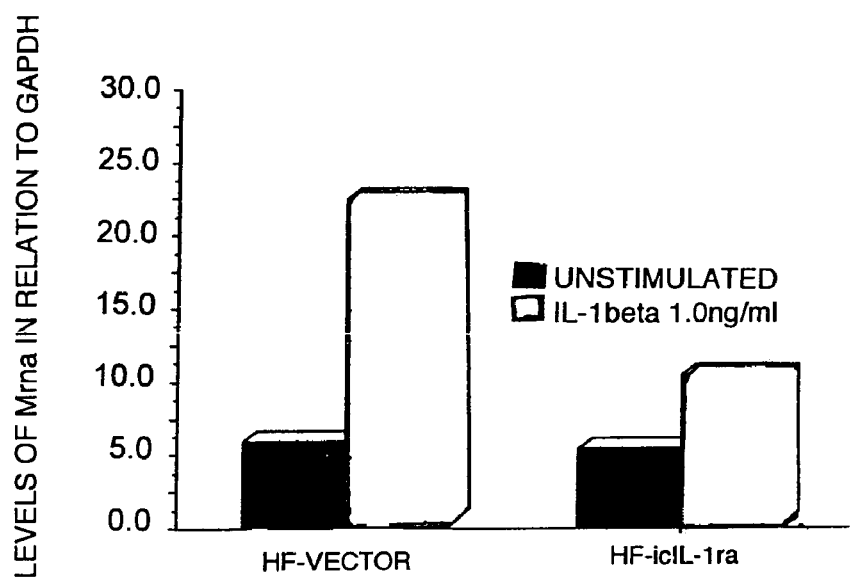

FIGS. 22A-C show reduced expression of MMP-1 mRNA in fibroblasts over-expressing icIL-1r type 1. FIG. 22A shows infant foreskin fibroblasts transfected with icIL-1ra type 1 (HF-icIL-1ra) or control (HF-VECTOR) were stimulated with 1.0 ng/ml IL-1b, 5.0 or 15 ng/ml TNF-α (TNF-α 1 & 2 respectively) for 12-16 h. The fibroblasts were harvested, lysed in Tri-Reagent (Sigma Aldrich Chemicals, St. Louis, Mo.), and total RNA was extracted. cDNA was synthesized using Oligo dT and AMV reverse transcriptase (Promega, Madison, Wis.). Using specific primers listed in Table 1, MMP-1 and GAPDH messages were estimated by semi-quantitative RT-PCR. The experiments were repeated three times with similar results. The data are represented as the ratio of MMP-1 to GAPDH (the housekeeping gene). FIG. 22B shows results of a two-step real time RT-PCR performed by a fluorogenic 5' nuclease assay using TaqMan PCR reagents obtained from Applied Biosystems (Foster City, Calif.). The reactions were performed according to manufacture's protocol. Each sample was assayed in duplicate. The housekeeping gene GAPDH was used as a control to normalize the amount of RNA present in various test samples. Higher Ct ratios indicate lower levels of mRNA. FIG. 22C shows equal numbers of HF-Vector and HF-icIL-1ra were stimulated with hrIL-1b (1.0 ng/ml) or hrTNF-a (10.0 ng/ml), and the cells were harvested after 12-16 h. Total cellular RNA was isolated using Tri-Reagent. Labeled probes for housekeeping genes (GAPDH & L32) and MMP-1 were transcribed from respective linearized plasmids using T7 RNA polymerase in the presence of α$^{32}$P-UTP (RPA, Pharmingen). After hybridization and digestion, protected probes were resolved by PAGE on urea-acrylamide gel. The bands were visualized, and the intensities of the bands were quantified using a Bio-Rad Model GS-505 phosphor imager (Bio-Rad, Herculis, Calif., USA). The results are expressed after normalizing the intensities of MMP-1 bands from various samples to that of the housekeeping genes (GAPDH or L32) in respective samples.

Figure 23:
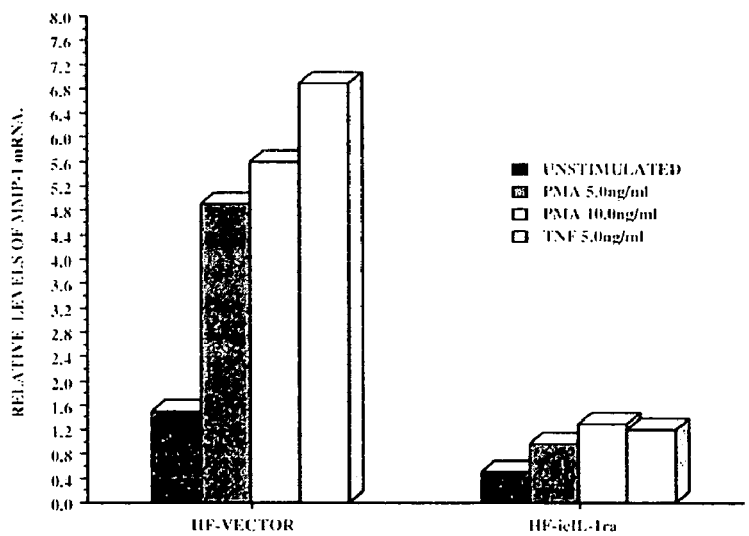
Figure 23:
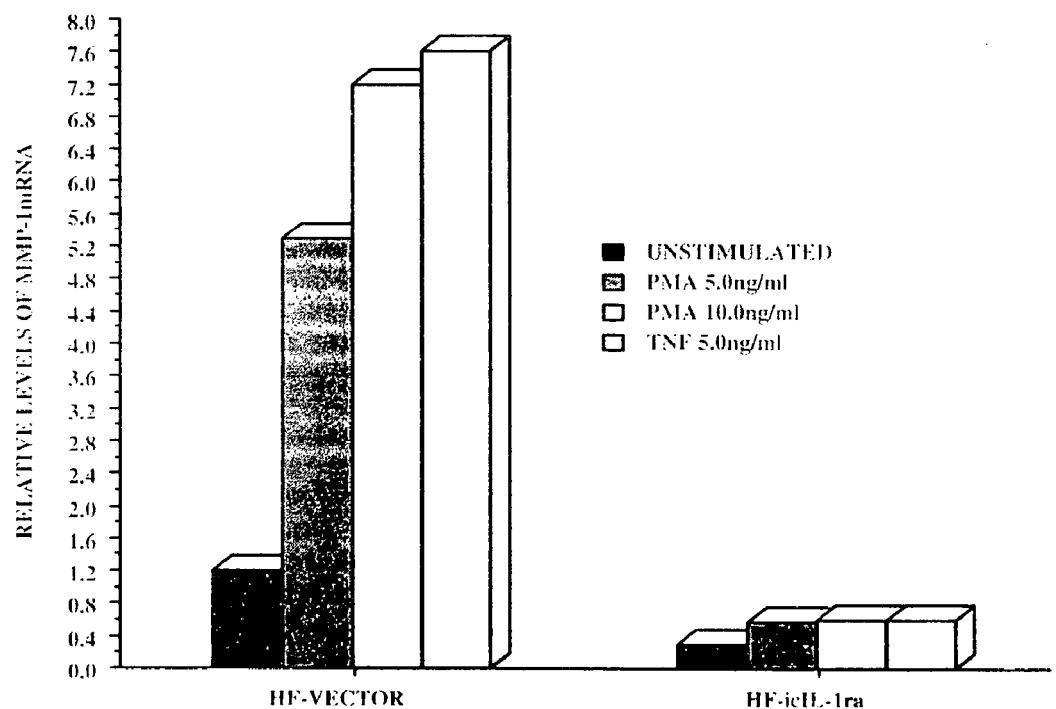

FIG. 23 shows reduced levels of MMP-1 mRNA in human fibroblasts over-expressing icIL-1ra type 1 upon exposure to PMA or TNF-a. Equal numbers of fibroblasts were seeded in 12-well plates. Once the cells were attached and the cell monolayers reached 80% confluence, fibroblasts were stimulated for 12-16 hr with TNF-α (10 ng/ml) or PMA (5 ng/ml or 10 ng/ml). Total RNA was then harvested using Tri-Reagent. Messenger RNA was reverse transcribed using AMV reverse transcriptase and oligo dT (Promega, Madison, Wis.). The cDNAs were amplified by polymerase chain reaction (PCR) using specific sets of primers (Table 1). The PCR products were run on a 2% agarose gel, and the gel was stained with ethidium bromide. The specific bands of each message were scanned, and the density of bands was measured using Alpha Innotech Imaging System (Foster City, Calif.). The bar graphs represent values expressed as ratios of MMP-1 message to that of the housekeeping gene GAPDH. Data are shown for two separate experiments.

Figure 24:
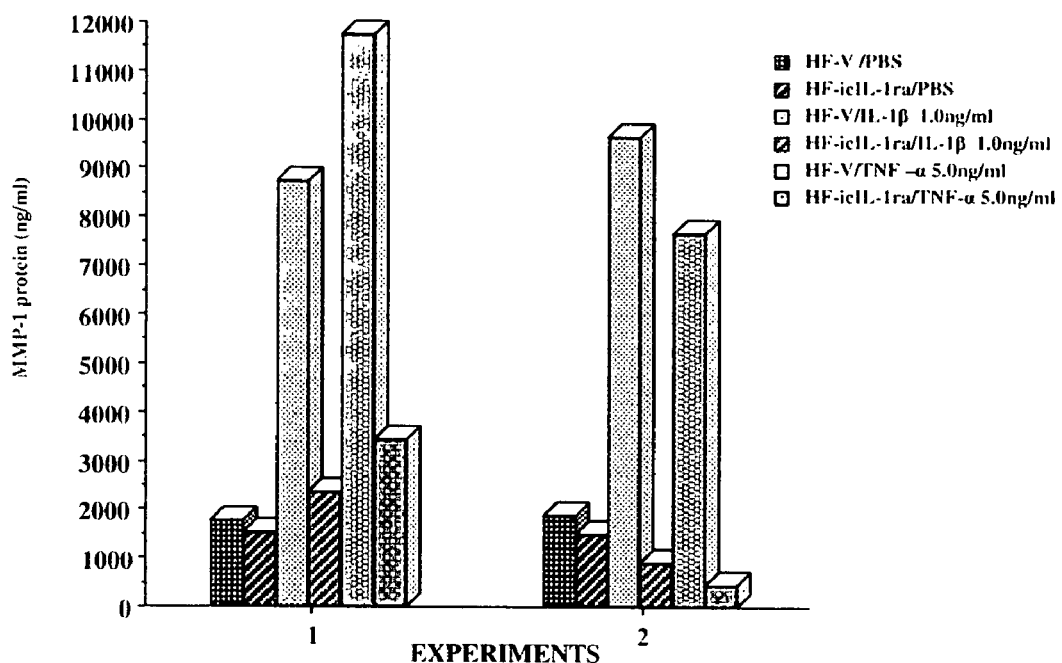

FIG. 24 shows reduced levels of MMP-1 protein in human fibroblasts over-expressing icIL-1ra type 1. MMP-1 protein secreted into the culture medium was measured by ELISA. After 48 h treatment with hrIL- 1β or hrTNF-α, culture supernatants were collected and cleared by centrifugation at 18000× g for 30 min at 4° C. Cleared supernatants were treated with protease inhibitors and stored at −80° C. until tested.

Figure 25:
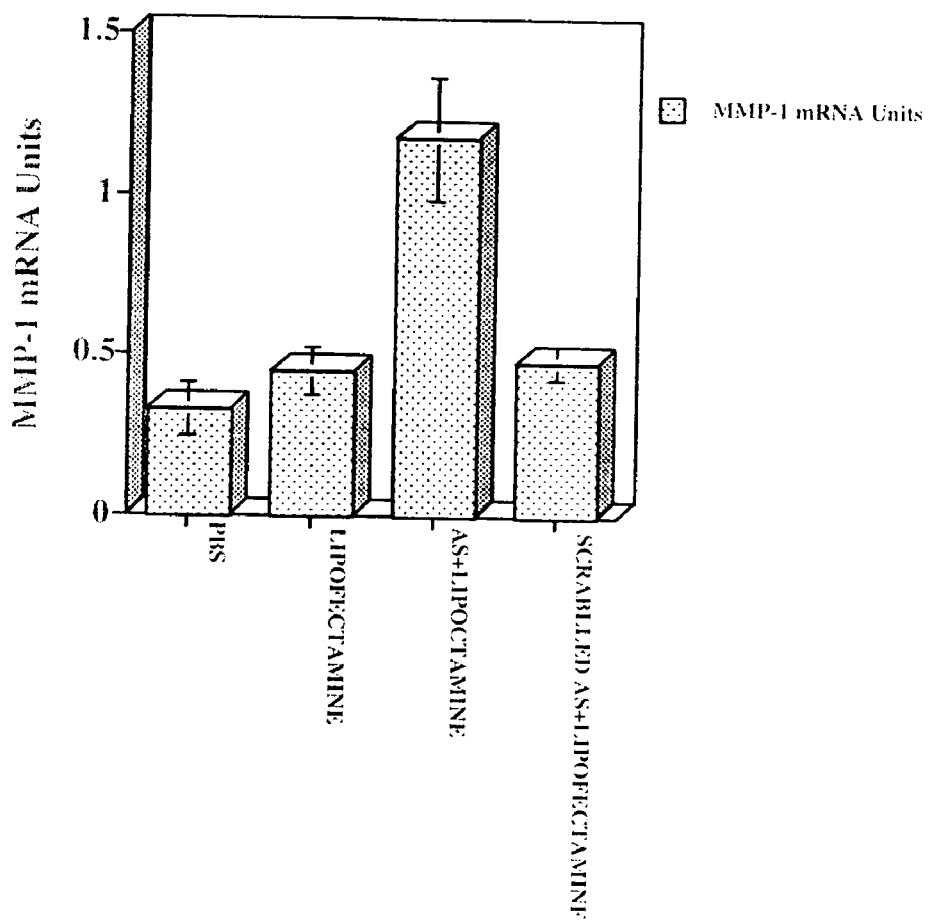

FIG. 25 shows human fibroblasts transfected with icIL-ra type 1 and treated with antisense oligonucleotide directed towards icIL-1ra type 1 upregulate MMP-1 mRNA when stimulated with IL-1β. Phosphorothioate-derivatized antisense oligodeoxynucleotide complimentary to −6 to +12 of the natural icIL-1ra was synthesized and purified by HPLC Integrated DNA Technologies Inc. (Coralville, Ind.). As a control, antisense oligonucleotide with a scrambled sequence was prepared by a similar method. Fibroblasts over-expressing icIL-1ra type 1 were transfected with 300 mM of antisense icIL-1ra type 1 oligonucleotide (24 h prior to stimulation with 100 pg/ml of IL-1 beta) using LipofectAMINE™ protocol. PBS and LipofectAMINE™ alone served as additional controls. The cells were harvested 12-18 h after stimulation for RNA extraction. Total RNA was reverse transcribed and MMP-1 mRNA was estimated by semi-quantitative RT-PCR.

Figure 26A:
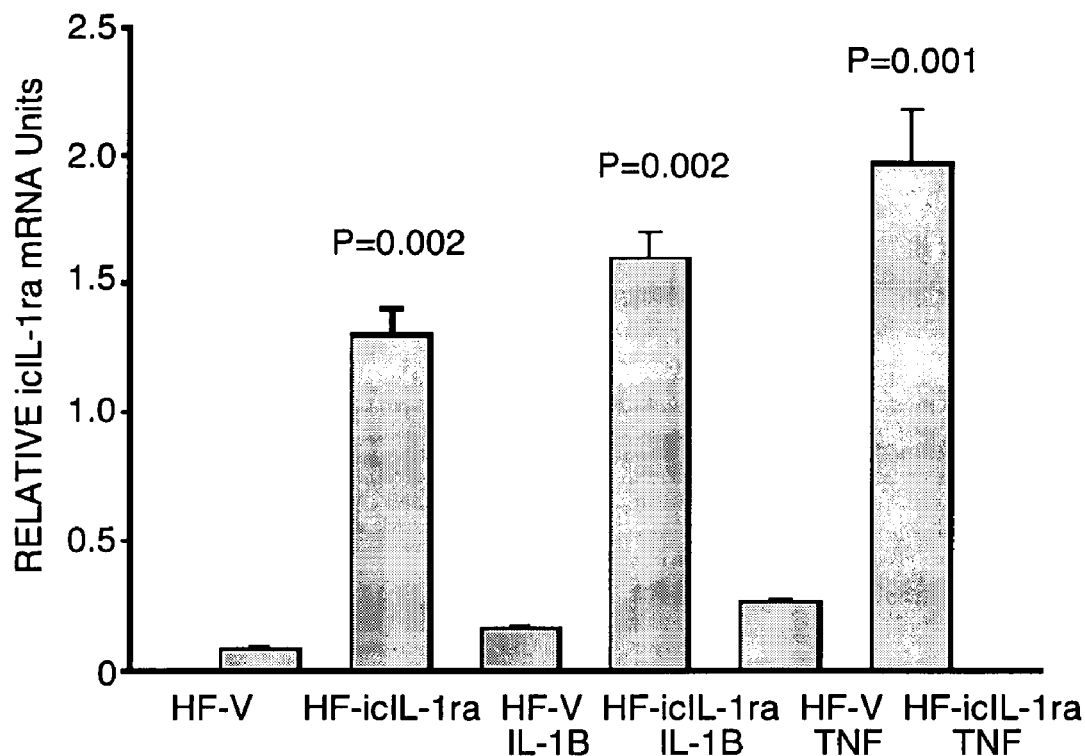
Figure 26B:
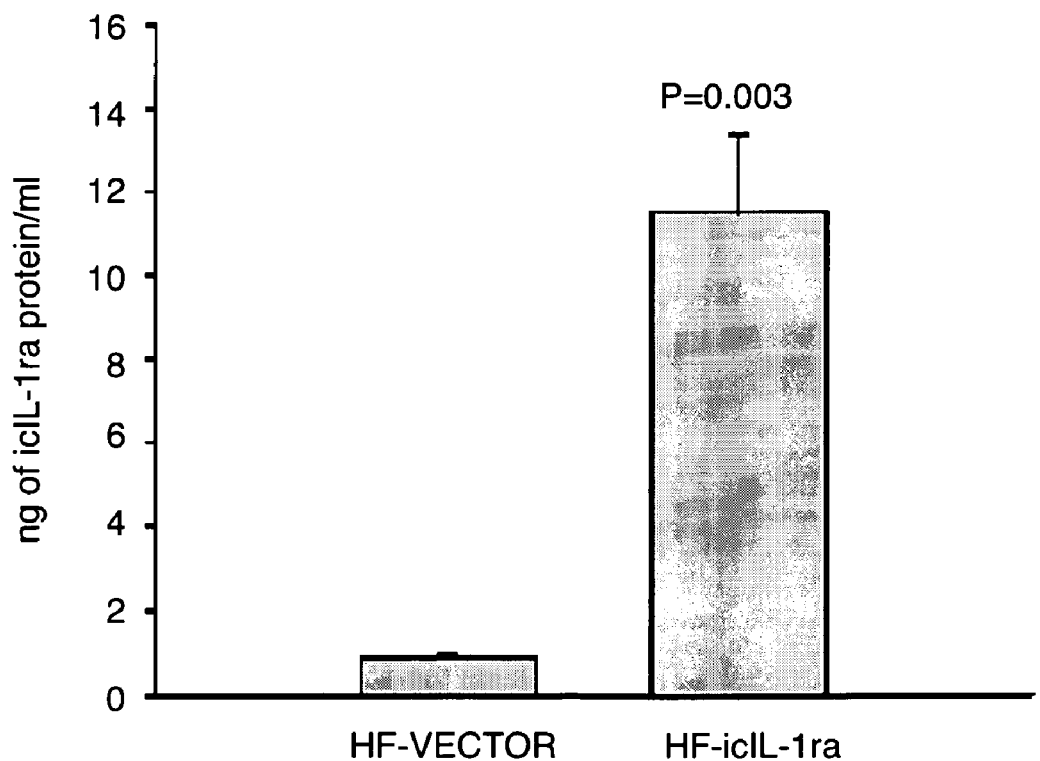

FIG. 26A-B show over-expression of icIL-1ra in fibroblasts transfected with plasmid encoding icIL-1ra. FIG. 26A shows results of RT-PCR where equal number of cells (HF-icIL-1ra and HF-vector) were stimulated with 0, 1.0 ng of hrIL-1β or 10 ng/ml of hrTNF-α. After 24 h, total RNA was extracted and mRNA levels of icIL-1ra and GAPDH were estimated by real time RT-PCR. FIG. 26B shows the results of ELISA where equal numbers of HF-icIL-1ra and HF-Vector fibroblasts maintained in complete DMEM for 48 h were harvested and lysed. The clarified cell lysates were tested for icIL-1ra type 1 by ELISA. The error bars indicate mean±SD of three separate experiments on the same batch of stably transfected fibroblasts.

Figure 27A:
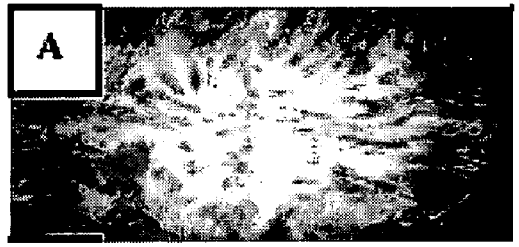
Figure 27B:
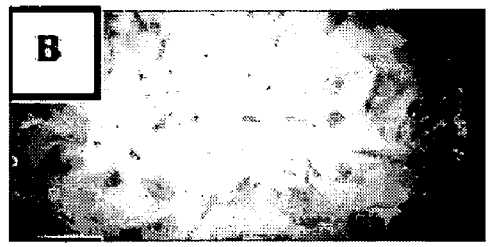
Figure 27C:
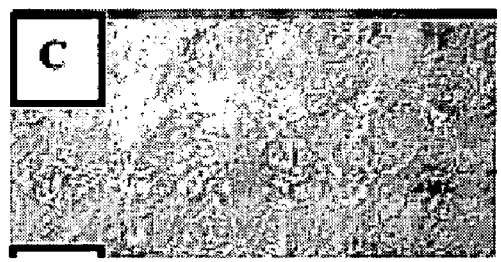
Figure 27D:
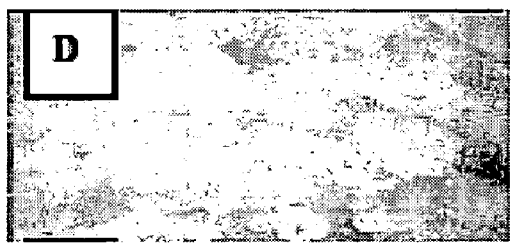
Figure 27E:
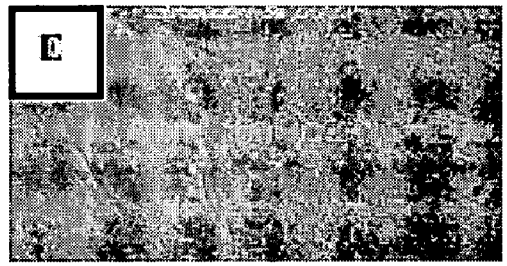
Figure 27F:
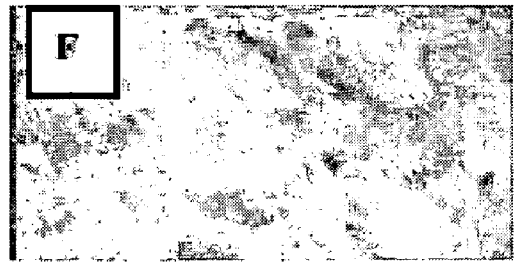

FIG. 27A-F show myofibroblast-like morphology of icIL-1ra transfected fibroblasts. FIG. 27A shows control fibroblasts (HF-Vector) with normal spindle-shaped fibroblast morphology after maintaining in complete DMEM for 6 week with medium change once in 5 days. FIG. 27B shows fibroblasts over expressing icIL-1ra (HF-icIL-1ra) with myofibroblast-like morphology. Cells were fixed and permeabilized (cytofix/cytoperm) and were subjected to immunoperoxidase staining with mouse anti-human α-SMA (Sigma) clone 1A4 monoclonal antibody followed by color reaction developed by streptavidin-horseradish-peroxidase system. Cells were visualized under phase contrast microscopy after Coomassie brilliant blue staining. FIGS. 27C and 27D show HF-Vector with little α-SMA staining; FIGS. 27E and 27F show HF-icIL-1ra with α-SMA staining.

Figure 28:
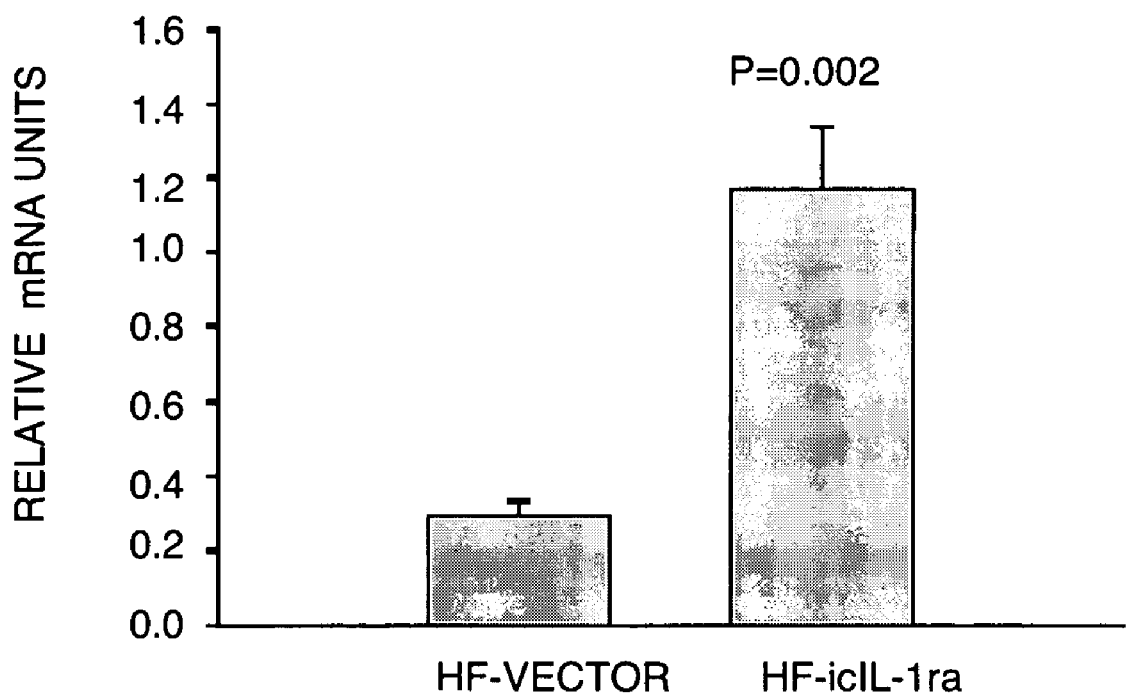

FIG. 28 show enhanced levels of α-SMA mRNA in icIL-1ra over expressing fibroblasts. Fibroblasts overexpressing icIL-1ra (HF-icIL-1ra) and control fibroblasts (HF-Vector) were maintained in complete DMEM for 6 week with a medium change once every 5 days. Cells were harvested and total cellular RNA was extracted and reverse transcribed. The cDNA thus obtained was amplified and quantified by real-time PCR. The values are expressed as ratios of Ct values for α-SMA to that of the Ct value of GAPDH. The values indicate mean±SD of three independent experiments performed on same batch of stably transfected fibroblasts.

Figure 29:
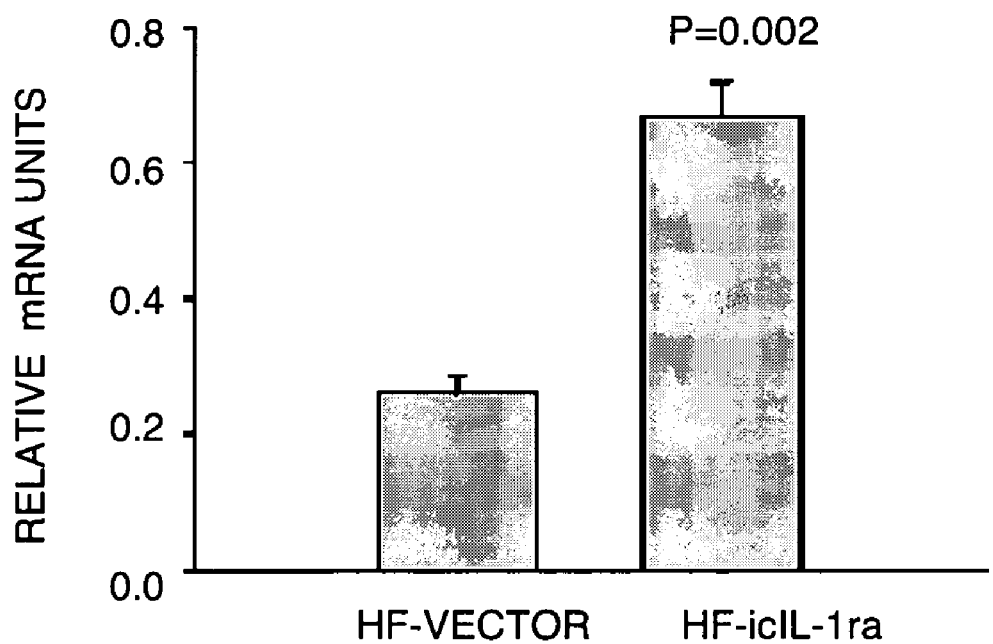

FIG. 29 shows enhanced levels of PAI mRNA in icIL-1ra over expressing fibroblasts. Plasminogen activator inhibitor (PAI) mRNA levels were assessed by real time RT-PCR on cDNA obtained from the same fibroblasts used for α-SMA estimation. The values are expressed as ratios of Ct values for PAI to that of Ct value of the housekeeping gene GAPDH. The values indicate mean±SD of three independent experiments performed on same batch of stably transfected fibroblasts.

Figure 30:
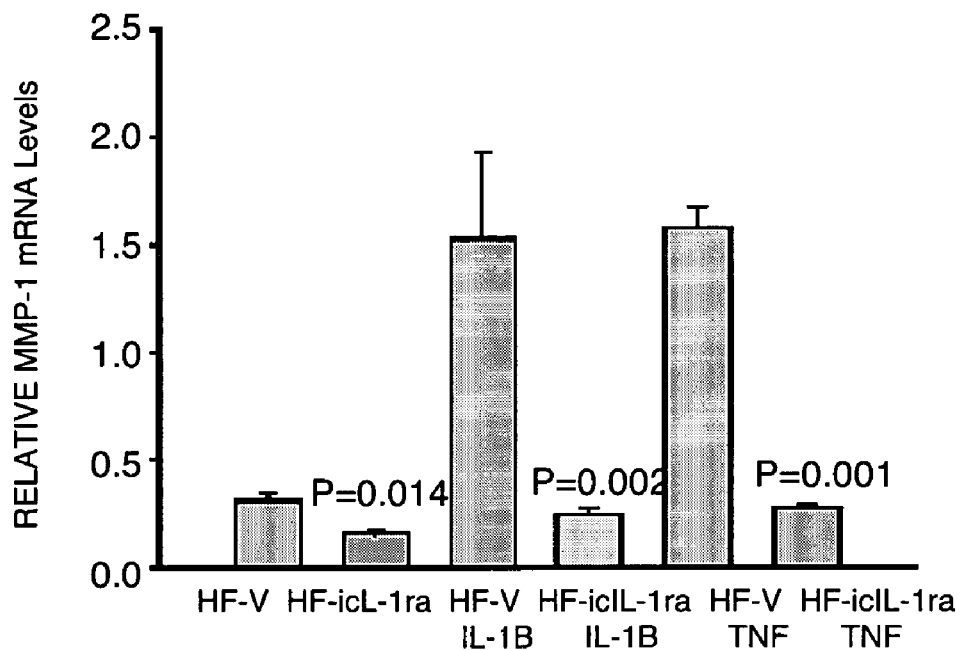

FIG. 30 shows reduced expression of MMP-1 mRNA in fibroblasts overexpressing icIL-1ra. Infant foreskin fibroblasts were transfected with icIL-1ra type 1 (HF-icIL-1ra) and control (HF-Vector) was stimulated with 1.0 ng/ml IL-1β or 10 ng/ml TNF-α for 12-16h. MP-1 and GAPDH message levels were estimated using real-time RT-PCR. Three separate experiments were performed on same batch f stably transfected fibroblasts. The results are represented as the reciprocal of the ratios of the Ct values of MMP-1 to GAPDH.

Figure 31:
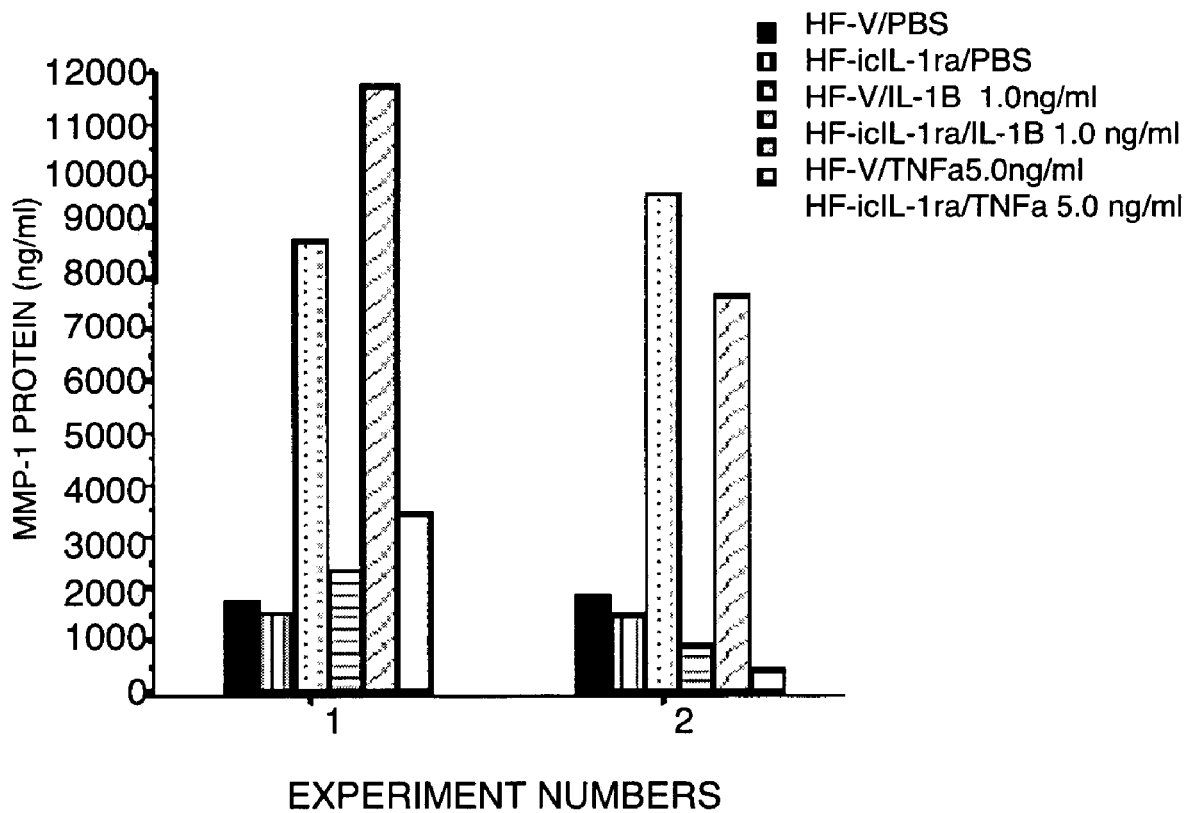

FIG. 31 shows reduced level of MMP-1 protein in human fibroblasts over expressing icIL-1ra type 1. Fibroblasts were cultured for 48 h with hrIL-1β (1.0 ng/ml) or hrTNF-α (5 ng/ml) and MMP-1 protein secreted into the culture medium was measured by ELISA.

Figure 32:
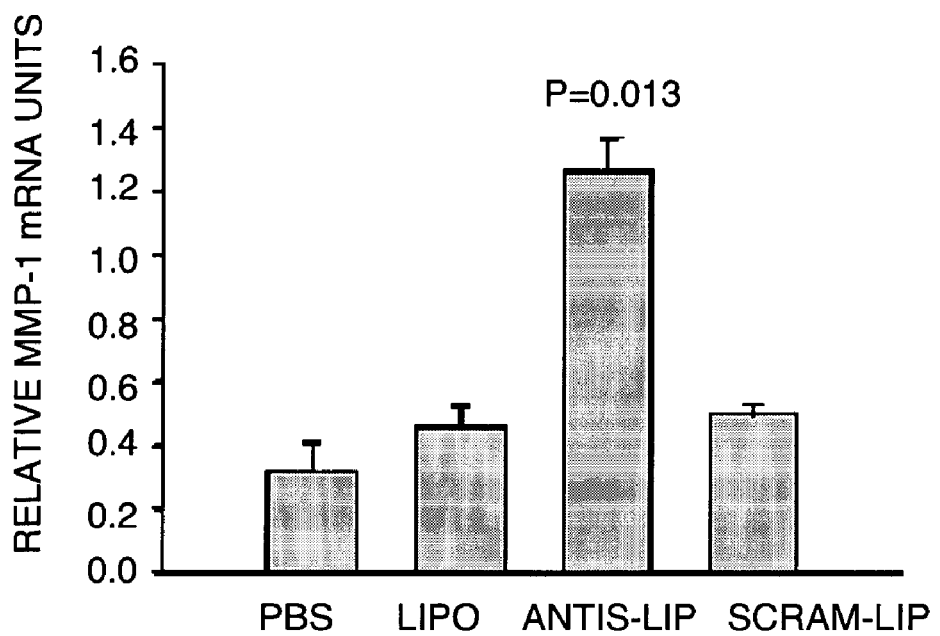

FIG. 32 shows human fibroblasts transfected with icIL-1ra type 1 and treated with antisense oligonucleotide directed towards icIL-1ra upregulates MMP-1 mRNA when stimulated with IL-1β. Fibroblasts over-expressing icIL-1ra type 1 were transfected with different concentrations of antisense icIL-1ra type 1 oligonucleotide (24 h prior to stimulation with IL-1β) using LipofectAMINE. PBS alone, LipofectAMINE alone and treatment with oligonucleotide having scrambled sequence served as controls. The cells were harvested 12-18 h after stimulation for RNA extraction. Total RNA was reverse transcribed and MMP-1 mRNA was estimated by real time RT-PCR. The values indicate mean±SD of three independent experiments performed on same batch of transfected geneticin selected fibroblasts (LIPO: LipofectAMINE alone, ANTIS-LIP: Antisense icIL-1ra oligonucleotide+LipofectAMINE, SCRAM-LIP: Scrambled oligonucleotide+LipofectAMINE).

Figure 33:
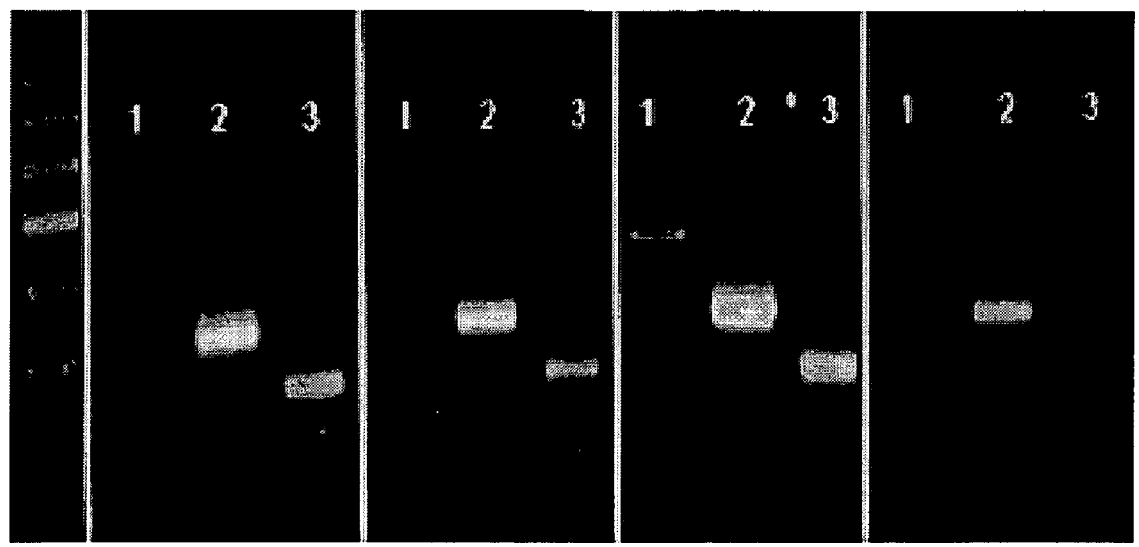

FIG. 33 shows that icIL-1ra expression downregulates c-fos and c-jun mRNA expression. Twenty-four hours prior to stimulation with IL-1β, fibroblasts over-expressing icIL-1ra (HF-icIL-1ra) were treated with (A) PBS, (B) LipofectAMINE, (C) LipofectAMINE+antisense oligonucleotide directed against icIL-1ra mRNA and (D) LipofectAMINE+ scrambled oligonucleotide. Total RNA was isolated 6 h after IL-1β stimulation, reverse transcribed and the cDNA was amplified using specific primers. THE PCR products obtained from the exponential phase of amplification (28-32 cycles) was analyzed on 2% agarose gel and stained with ethidium bromide. Lanes 1: c-fos, 2: c-jun, 3: Jun B. The experiment was performed two times on the same batch of stably transfected fibroblasts. M: PCR Markers (2000 bp-50 bp).

Figure 34:
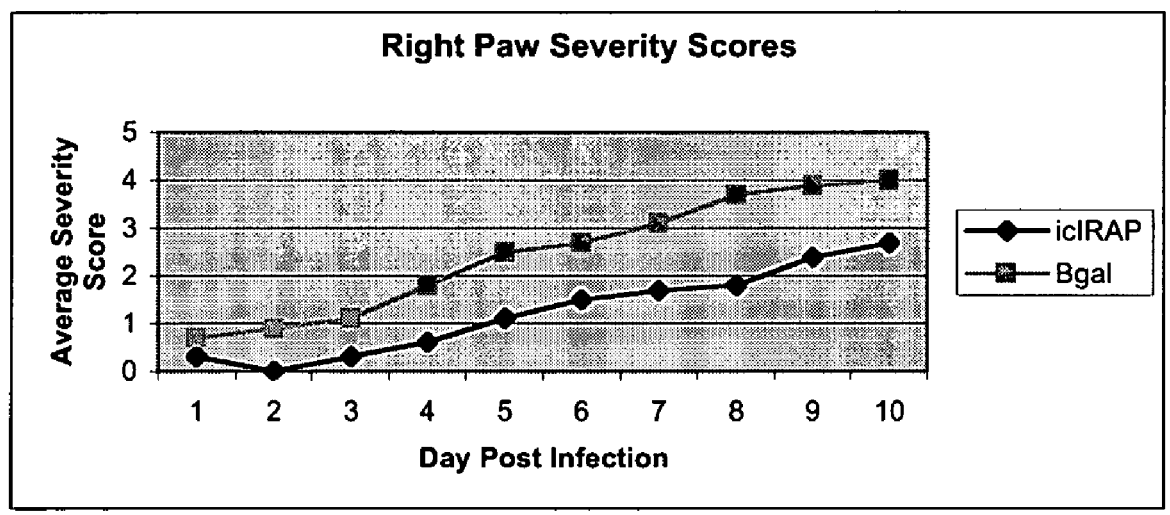

FIG. 34 shows that icIL-1ra plays an important role in suppressing experimental autoimmune arthritis pathway. DBA/1-QCII24 transgenic mice for a type II collagen T cell receptor were immunized with type II collagen and seven days later one of the hind paw was injected with an adenoviral vector containing cDNA encoding the predominant form of icIL-1ra. The right paw severity scores of mice injected with beta-galactosidase were compared with the paws of the mice injected with icIL-1ra.

DETAILED DESCRIPTION OF THE INVENTION

Matrix metalloproteinase (MMPs) are important inflammatory enzymes that are directly involved in degradation of matrix and considered as one of the key factors in arthritis induction. Therefore lowering matrix metalloproteinase levels can be a way to protect cartilage and inhibit arthritis. The present invention has demonstrated that SSc fibroblasts constitutively express intracellular preIL-alpha and also exhibit enhanced upregulation of icIL-1ra after stimulation by IL-1beta or TNF alpha. It has also extended the observation of decreased basal collagenase in SSc fibroblasts by demonstrating the refractoriness of MMP-1 to induction by IL-1 beta and TNF alpha in these cells as compared to normal fibroblasts. Further, when normal fibroblast were transduced to constitutively express preIL-1 alpha, these fibroblasts also exhibited the same enhanced upregulation of icIL-1ra and same defect in Mmp-1 induction as in SSc fibroblasts. Further, the present invention demonstrated a relationship between intracellular preIL-1 alpha and icIL-1ra in modulating fibroblast responses to exogenous IL-1. Specifically, the normal fibroblast constitutively expressing icIL-1ra show the same defect in MMP-1 production as SSc fibroblast. Thus, the data presented below show that the intracellular isoform of IL-1 receptor antagonist can repress the expression of collagenase (MMP-1) stimulated by potent inflammatory cytokines such as IL-1β or TNF-a.

Based on this observation, it is also contemplated to characterize the inhibition of collagenase gene expression in scleroderma (SSC) fibroblasts. For this, the level and time course of the production of mRNA MMP-1 in SSc fibroblasts from involved and uninvolved skin and normal fibroblast following stimulation with TNF alpha and PMA is correlated. Expression of MMP-1 and icIL-1ra will be quantitated in isolated RNA using ribonuclease protection probes. Further, the level and degree of inhibition of collagenase expression with regard to transcriptional or translational control in SSc fibroblasts is compared to the induction in normal fibroblasts.

Differences in the mRNA stability of MMP-1 is also determined in SSc and normal fibroblasts.

Collagenase is a matrix metalloproteinase that is involved in the degradation of collagen. The intracellular isoform of IL-1 receptor antagonist inhibits collagenase expression through the blocking of phosphorylation of c-jun-N-terminal kinase (JNK) and its downstream signaling pathways. Hence, the intracellular isoform of IL-1 receptor antagonist plays an important role in the control of cartilage degradation.

The involvement of c-fos, c-jun and JunB in transcriptional regulation of MMP-1 was demonstrated in the present invention. These data suggest that icIL-1ra affects the levels of transcription factors thereby contributing to the reduction in IL-1-induced Mmp-1 production in human fibroblasts. Further, the amount and activity of Ap-1 complexes present in stimulated cells is determined. Additionally, the ability of fos and Jun family members to bind to the two Ap-1 sequences, which are active in the Mmp-1 promoter, is also determined. The levels of other genes known to affect collagenase expression using DNA microarray analysis of mRNA from stimulated and unstimulated cultures of normal and SSc fibroblasts will also be surveyed.

Matrix metalloproteinases are major mediators of tissue destruction in chronic inflammatory disorders such as arthritis, degenerative intervertebral disc disorders and chronic skin ulcers in diabetic and bedridden patients. Results presented below indicate that over-expression of the intracellular isoform of IL-1 receptor antagonist by localized gene therapy would have dramatic effects by stopping tissue destruction in rheumatoid arthritis, other arthritides, degenerative intervertebral disc disease and in disorders such as chronic skin ulcers that occurs in diabetes mellitus and bed ridden patients.

Although a form of secreted isoform of IL-1 receptor antagonist called "anakinra" is currently approved by the FDA and marketed to treat rheumatoid arthritis, it is not very effective. Anakinra works solely by blockade of the cell surface receptors for IL-1 and does not enter the cell or have any intracellular functions. Currently, gene therapy using viral vectors has drawbacks; however, transfection of cDNA that is not virally delivered or integrated in the cellular DNA can be accomplished for topical applications such as bedsores, diabetic ulcers or peripheral vascular disease using a high-pressure delivery system ("Genegun"). The present invention has also demonstrated the effect on collagenase pathway using cDNA for icIL-1RA or with peptide fragments of icIL-1RA. Additionally using an antisense to icIL-1ra the present invention demonstrated the reversal of the effect of icIL-1ra.

Further, the observation that over-expression of icIL-1ra type I in normal fibroblasts induces a myofibroblast phenotype is novel and important to tissue repair and fibrosis. Myofibroblasts are abundant in granulation tissue of healing wounds, in organs undergoing fibrosis such as lung, kidney, liver, bone marrow and eye (Schmidt-Graff and Desmouliere, 1994). They also comprise a large portion of fibroblasts in dermal lesions of SSc. They are also known to express plasminogen activator inhibitor (Chuang-Tsai et al., 2003). The present invention demonstrated that overexpression of icIL-1ra induced a myofibroblast phenotype with characteristic morphology and enhanced expression of α-SMA and PAI. Hence, the mechanism involved in icIL-1ra mediated upregulation of α-SMA and myofibroblast differentiation will also be studied.

The present invention is directed to a method of inhibiting tissue degradation by contacting a cell in a tissue with an intracellular isoform of IL-1 receptor antagonist and inhibiting the expression of matrix metalloproteinase via the contact, thereby inhibiting the tissue degradation. This contacting step comprises over-expressing a gene encoding the intracellular isoform of IL-1 receptor antagonist in the cell or administering peptides of the intracellular form of IL-1 receptor antagonist to the target tissue. Such a method inhibits expression of a matrix metalloproteinase such as collagenase. As used herein, the term "contacting" refers to any suitable method of bringing an antagonist into contact with IL-1 receptor. In in vitro or ex vivo, this is achieved by exposing cells expressing IL-1 receptor to the antagonist in a suitable medium. For in vivo applications, any known method of administration is suitable.

In general, the gene encoding the intracellular IL-1 receptor antagonist is delivered by a viral vector such as adenoviral vector or by a non-viral gene delivery system such as high-pressure gene delivery system ("Genegun"). Other non-viral methods of gene delivery include, but are not limited to, electroporation (Tur-Kaspa et al., Mol. Cell Biol. 6:716-8 (1986); Potter et al., PNAS 81:7161-5 (1984)), direct microinjection (Harland et al., J Cell Biol. 101:1094-9 (1985)), DNA-loaded liposomes (Nicolau et al., Biochim. Biophys. Acta. 721:185-90 (1982); Fraley et al., PNAS 76:3348-52 (1979)), and receptor-mediated transfection (Wu and Wu, J Biol. Chem. 262:4429-32 (1987); Wu and Wu Biochemistry 27:887-92 (1988)). Additionally, the intracellular isoform of IL-1 receptor antagonist peptides have sequence of SEQ ID Nos. 13, 14, 15, 16, 17, 18 or are fragments thereof. The peptide fragment has the sequence of SEQ ID Nos. 19, 20, 21, 22, 23 or 24. Further, the tissue degradation is a component of chronic inflammatory disorder such as rheumatoid arthritis, degenerative intervertebral disc disease and chronic skin ulcers.

In another embodiment, there is provided a method of treating an individual having a chronic inflammatory disorder such as rheumatoid arthritis, degenerative intervertebral disc disease or chronic skin ulcers. The method involves over-expressing a gene encoding an intracellular isoform of IL-1 receptor antagonist in a target tissue or administering peptides of intracellular isoform of IL-1 receptor antagonist to the individual. In order to effect expression of the intracellular antagonist, constructs encoding the antagonist must be delivered into a cell. Various methods of gene delivery are known in the art. For example, a preparation comprising a physiologically acceptable carrier and a naked polynucleotide coding for an intracellular isoform of IL-1 receptor antagonist can be introduced into the interstitial space of a tissue comprising the cell, whereby the naked polynucleotide is taken up into the interior of the cell and has a physiological effect. In another embodiment, the transfer of a naked polynucleotide may be proceeded via particle bombardment, said particles being DNA-coated microprojectiles accelerated to a high velocity that allows them to pierce cell membranes and enter cells without killing them (Klein et al., Curr. Genet. 17:97-103 (1990)). In a further embodiment, the polynucleotide of the invention may be entrapped and delivered in a liposome (Ghosh and Bacchawat, Targeted Diagn. Ther. 4:87-103 (1991); Wong et al., Gene 10:87-94 (1980); Nicolau et al., Methods Enzymol. 149:157-76 (1987)). Additionally the peptides of intracellular isoform IL-1 receptor antagonist and fragments tthereof have the same sequence ID nos. as discussed above.

The following examples are given for the purpose of illustrating various embodiments of the invention and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Inhibition of Collagenase Expression In Pig Articular Chondrocytes By Intracellular Isoform of IL-1 Receptor Antagonist Chondrocytes were isolated from pig articular cartilage and cultured in monolayer. DNA encoding intracellular isoform of IL-1receptor antagonist and LacZ were subcloned into adenoviral vectors that were transfected into pig chondrocytes. Cells were infected with adenoviral vector 24 hours before stimulating with 10 ng/ml porcine IL-1β at a multiplicity of infection that gave a transfection efficiency of 90% as monitored by immunostaining with IL-1 receptor antagonist antibodies. Production of intracellular IL-1 receptor antagonist protein was determined by western blot analyses after transfection. Culture supernatants were removed and the cells were solubilized for Western blot analyses. Blots were scanned and quantitated using a Storm Phosphor Imaging detection system and computer-based image analysis software.

As shown in FIGS. 1-4, normal chondrocytes showed a huge increase of collagenase (MMP-1) expression after treatment with 10 ng/ml of porcine IL-1β or TNF-a, whereas chondrocytes over-expressing intracellular isoform of IL-1 receptor antagonist were able to inhibit that increase of collagenase protein.

Figure 1:
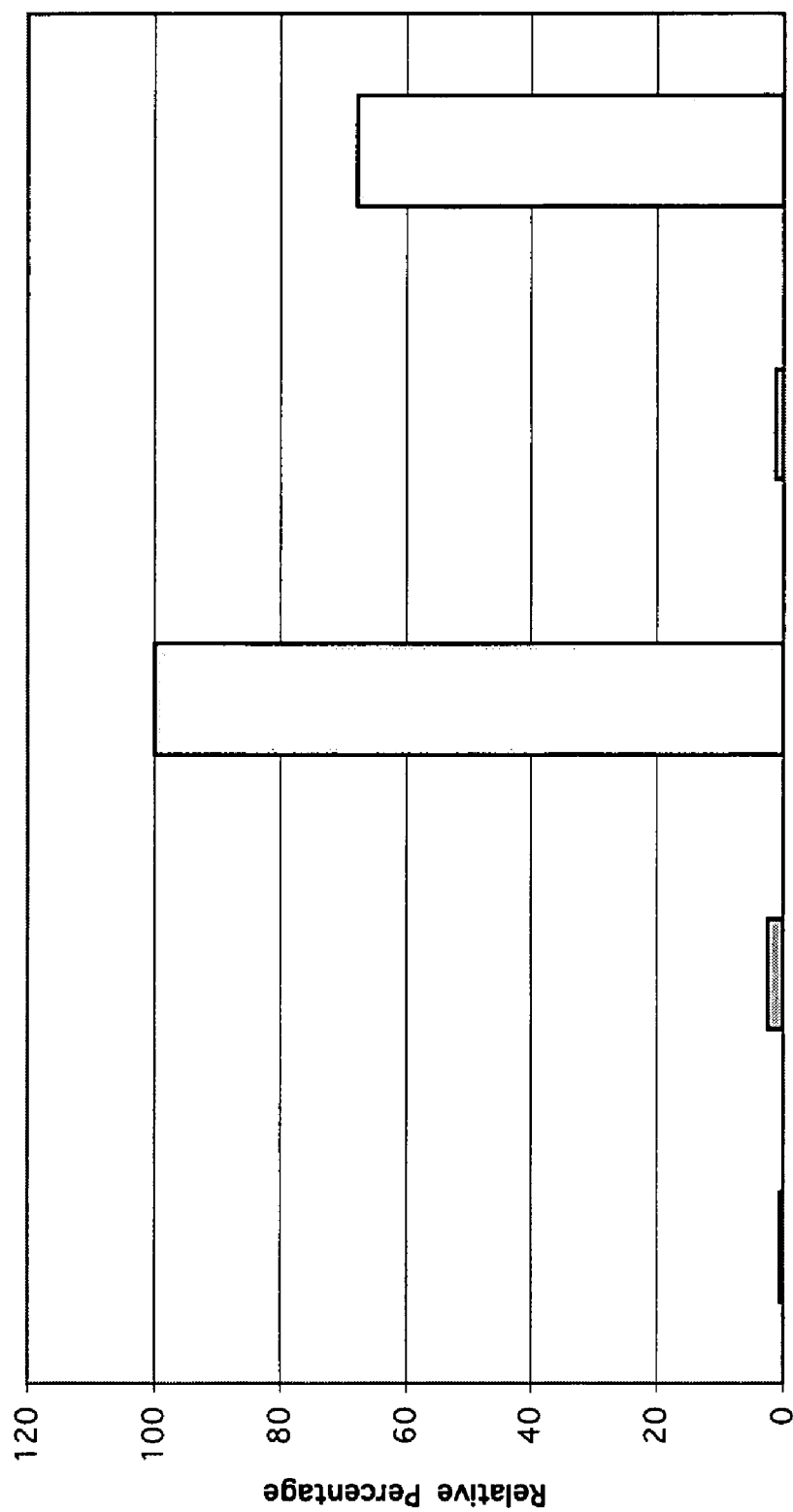
FIG. 1 shows RT-PCR analyses of collagenase (MMP-1) mRNA in pig chondrocytes transfected with adenoviral vectors containing cDNA encoding β-galactosidase (β-gal) or intracellular isoform of IL-1 receptor antagonist (icIL- 1ra). The cells were stimulated with 10 ng/ml of porcine IL-1β, and IL-1b-induced MMP1 mRNA was dramatically reduced in pig chondrocytes transfected with the intracellular IL-1 receptor antagonist.
Figure 2:
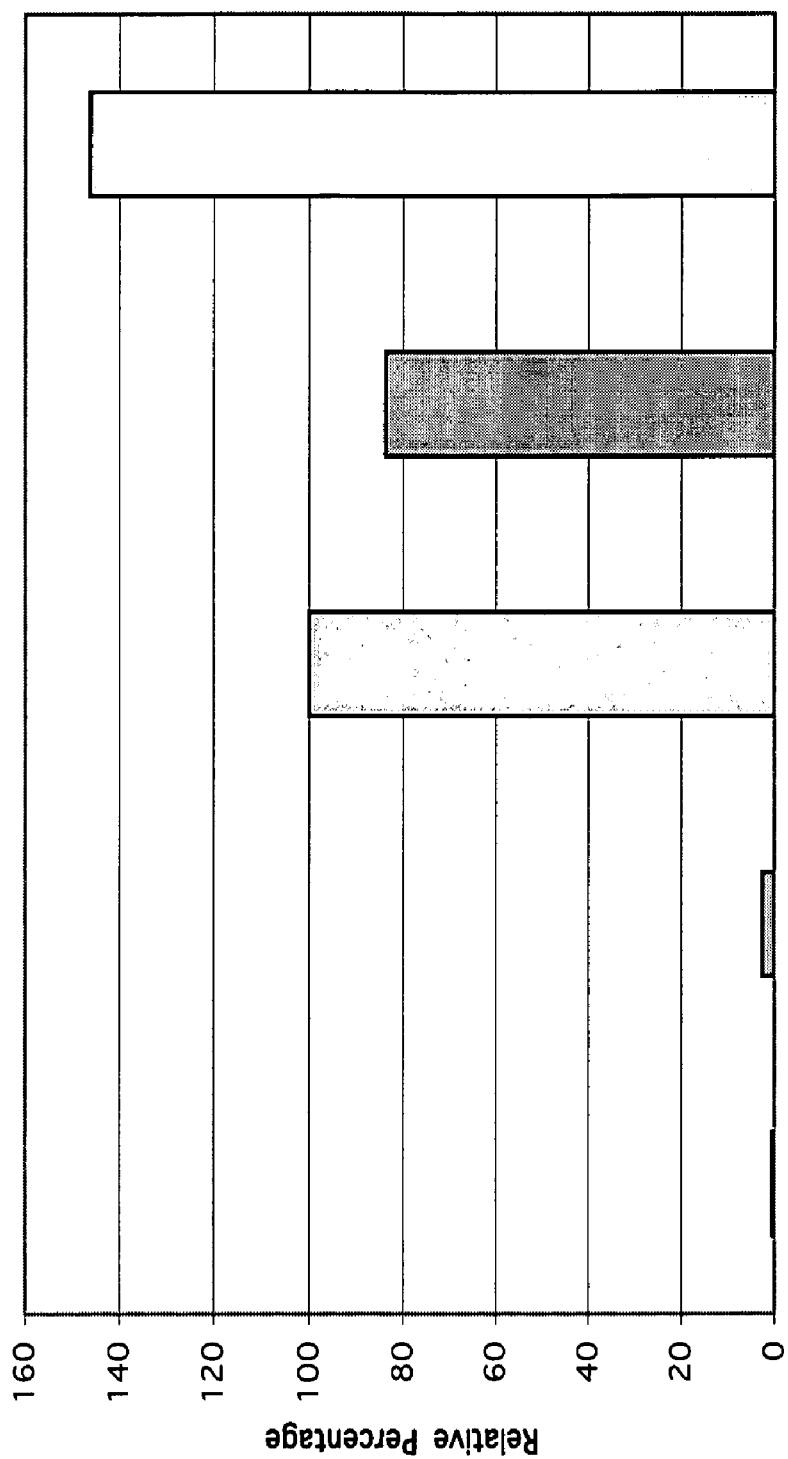
FIG. 2 shows RT-PCR analyses of collagenase (MMP-1) mRNA in pig chondrocytes transfected with adenoviral vectors containing cDNA encoding β-galactosidase (β-gal) or intracellular isoform of IL-1 receptor antagonist (icIL-1ra). The cells were stimulated with 10 ng/ml of TNF-α, and TNF-a-induced MMP1 mRNA was dramatically reduced in pig chondrocytes transfected with the intracellular IL-1 receptor antagonist.
Figure 3:
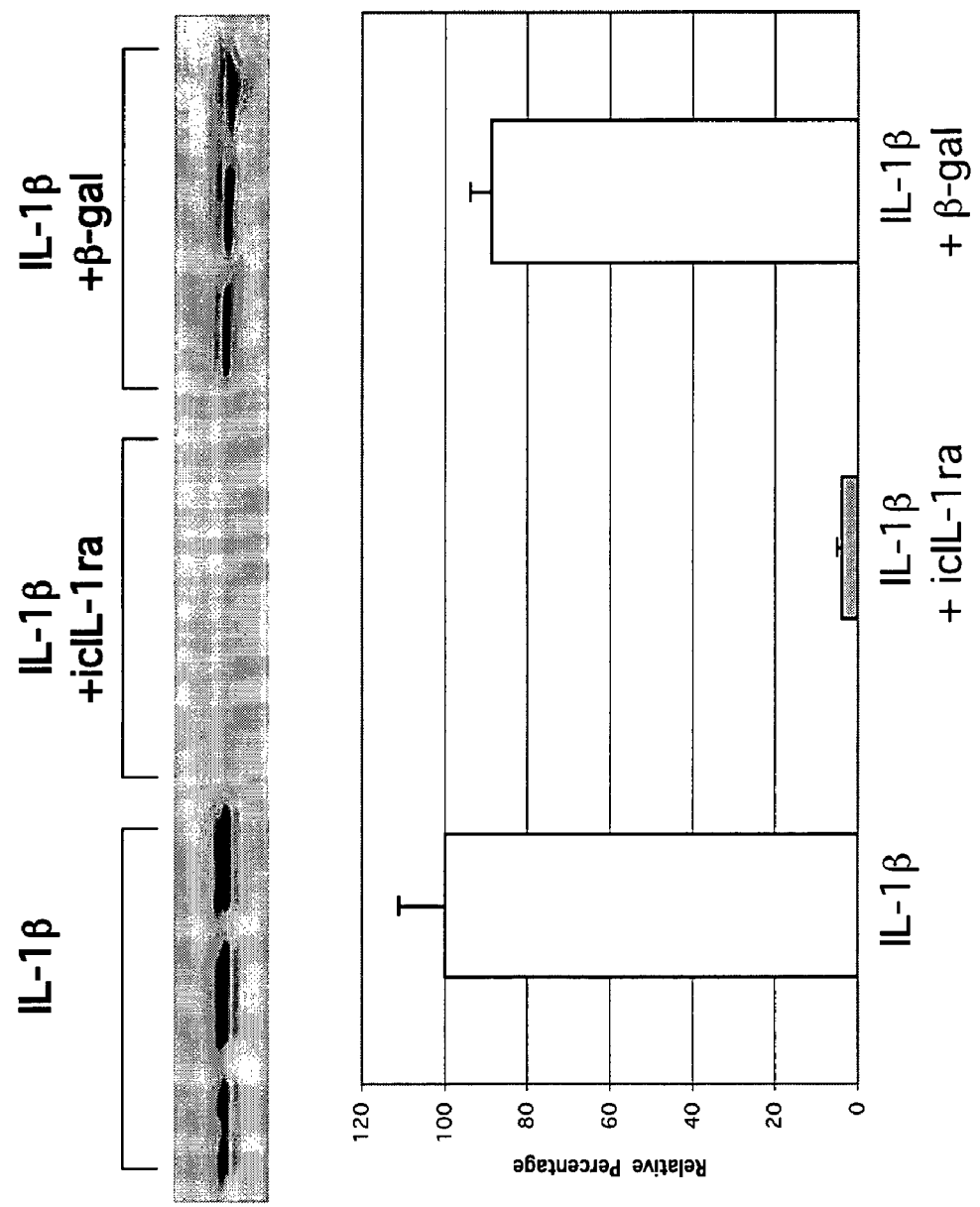
FIG. 3 shows Western blot analyses of collagenase (MMP-1) production in pig chondrocytes transfected with adenoviral vectors containing cDNA encoding β-galactosidase (β-gal) or intracellular isoform of IL-1 receptor antagonist (icIL-1ra). The cells were stimulated with 10 ng/ml of porcine IL-1β, and IL-1b-induced MMP1 protein were dramatically reduced in pig chondrocytes transfected with the intracellular IL-1 receptor antagonist.
Figure 4:
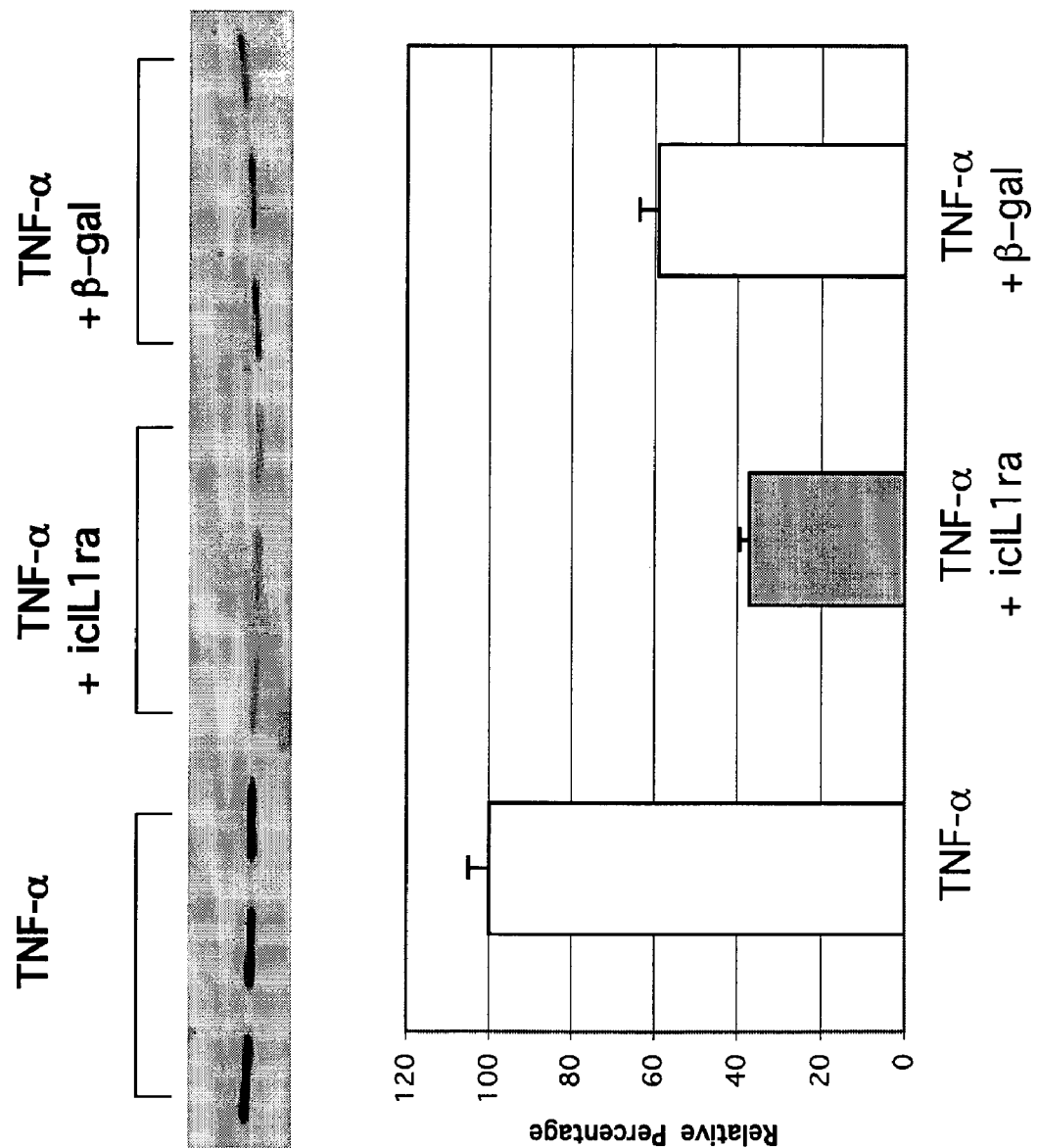
FIG. 4 shows Western blot analyses of collagenase (MMP-1) production in pig chondrocytes transfected with adenoviral vectors containing cDNA encoding β-galactosidase (β-gal) or intracellular isoform of IL-1 receptor antagonist (icL-1ra). The cells were stimulated with 10 ng/ml of TNF-α, and TNF-a-induced MMP1 protein were dramatically reduced in pig chondrocytes transfected with the intracellular IL-1 receptor antagonist.
Figure 5:
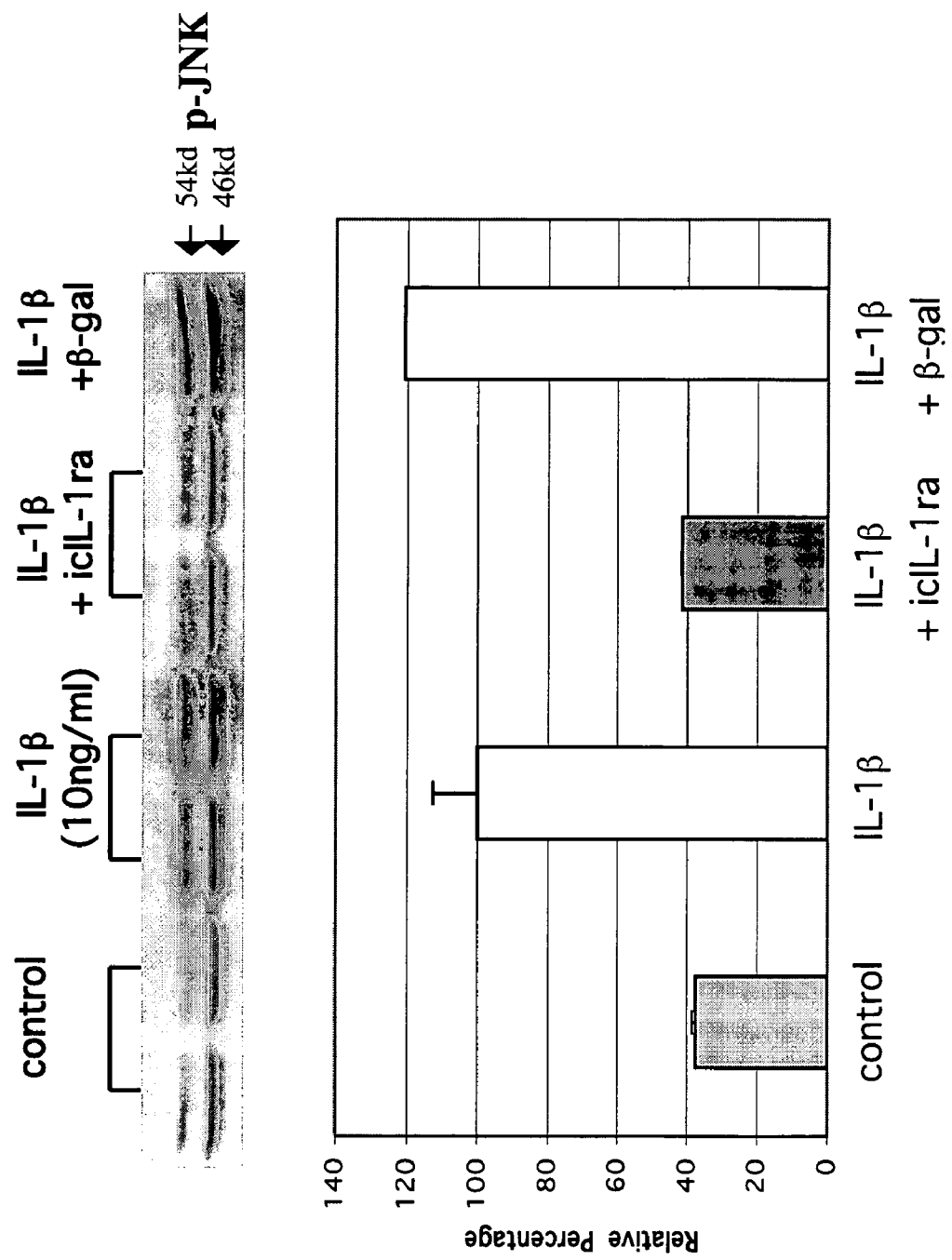
FIG. 5 shows Western blot analyses of phosphorylation of c-jun amino-terminal kinase (JNK) after stimulated with porcine IL-1b (10 ng/ml) for 15 minutes. The result indicates c-jun amino-terminal kinase phosphorylation was inhibited by intracellular isoform of IL-1 receptor antagonist (icIL-1ra).
Figure 6:
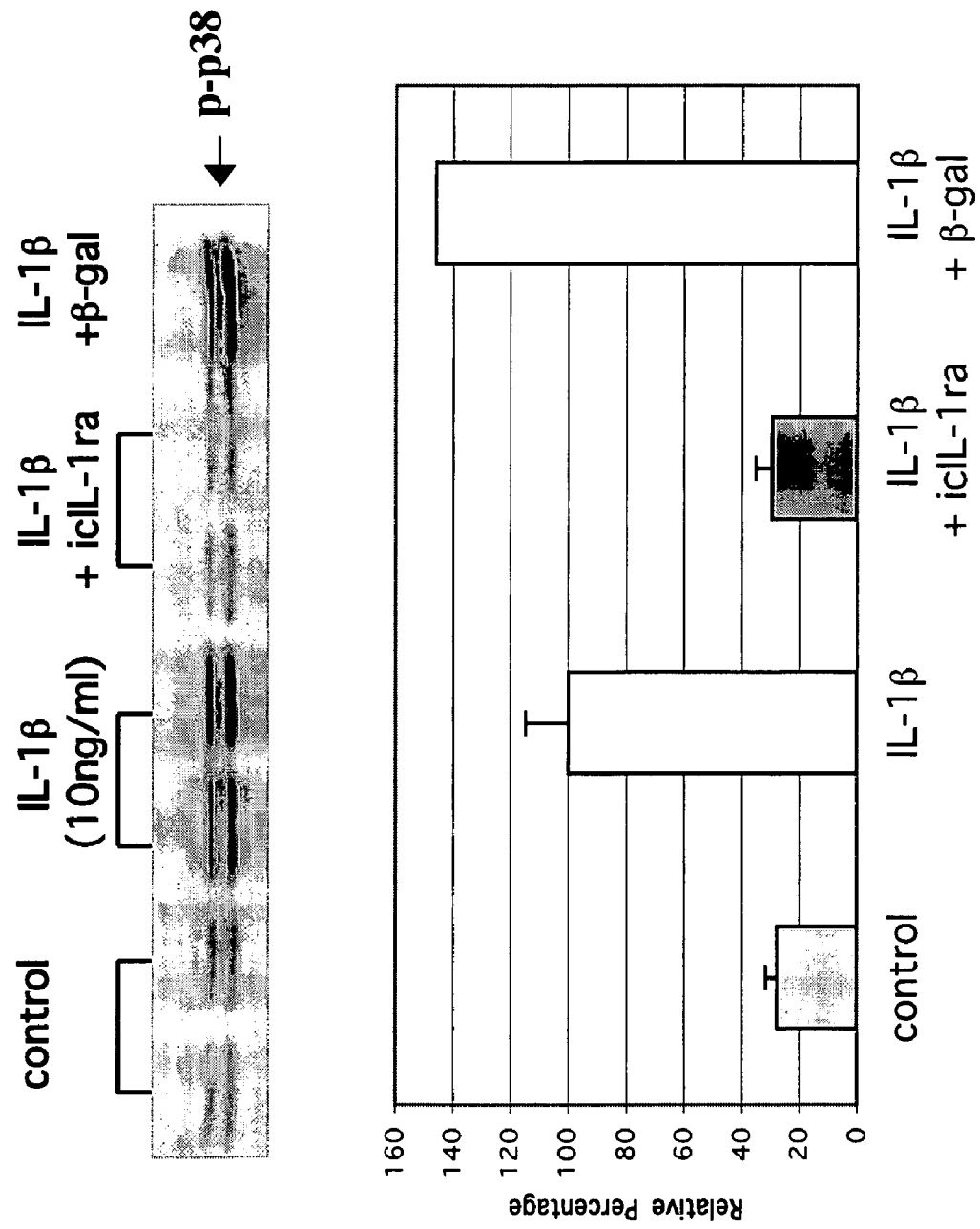
FIG. 6 shows Western blot analyses of phosphorylation of p-38 after stimulated with porcine IL-1b (10 ng/ml) for 15 min. The result indicates p38 MAP kinase phosphorylation was inhibited by intracellular isoform of IL-1 receptor antagonist (icIL-1ra).

Next, intracellular signaling was examined in order to determine the mechanism of collagenase inhibition by the intracellular isoform of IL-1 receptor antagonist. As shown in FIGS. 5-6, c-jun-N-terminal kinase (JNK) activity and p38 activation, which were increased by porcine IL-1β stimulation, were blocked by in cells transfected with the intracellular isoform of IL-1 receptor antagonist.

EXAMPLE 2

Impaired Collagenase Expression In Dermal Fibroblasts Explanted From Patients With Scleroderma Scleroderma is an immune-mediated disease (autoimmunity to matrix proteins and other antigens) characterized by excessive extracellular matrix deposition (particularly collagen) in skin and internal organs. Reduced collagenase activity may be one of the factors resulting in increased collagen deposition in the interstitium of the skin of patients with scleroderma. Hence, the present example examines the expression of collagenase in dermal fibroblasts obtained from patients with scleroderma.

Dermal fibroblasts were obtained from infant foreskins by conventional explant culture techniques and grown in Eagle's minimal essential medium (EMEM) containing Earl's balanced salt solution, 22 mM HEPES buffer, nonessential amino acids (NEAA), 0.05 mM sodium pyruvate, 2 mM L-glutamine, 100 U/ml penicillin, 100 ug/ml streptomycin, and 9% fetal bovine serum (FBS), hereafter referred to as "Complete EMEM". Dermal fibroblasts derived from explants of involved skin from scleroderma patients or from adult normal donors were explanted and maintained in RPMI 1640 (Invitrogen, Life Technologies, Gaithersburg, Md.) containing 100 U/ml penicillin, 100 µg/ml streptomycin, 10 ug/ml gentamicin, 22 mM HEPES, 0.05 mM sodium pyruvate, nonessential amino acids, 2 mM L-glutamine, 50 µM 2-mercaptoethanol, and 9% FBS hereafter referred to as "complete RPMI". Fibroblasts between 5 to 10 subpassages were used.

Figure 7:
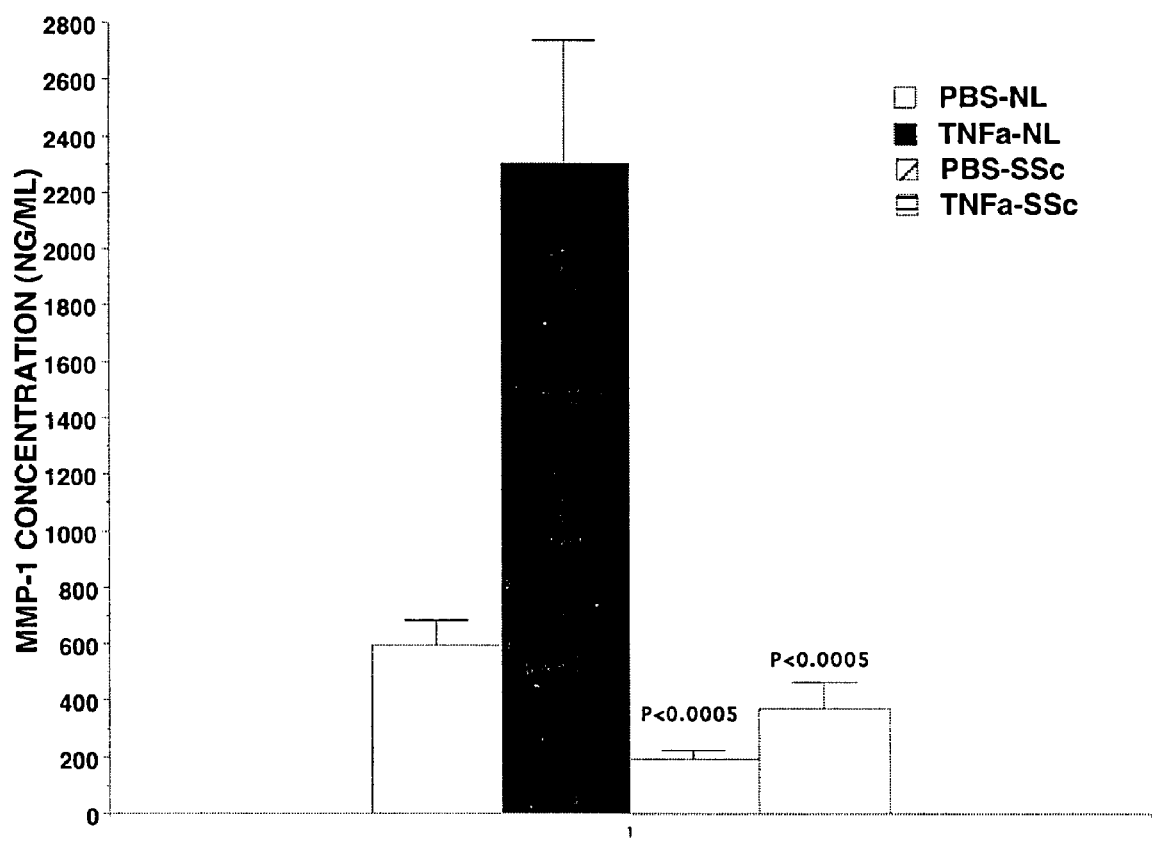
FIG. 7 shows dermal fibroblasts from patients with scleroderma (SSc) have reduced expression of MMP-1 in the presence and absence of TNF-α. Fibroblasts cultured from the skin of 7 normal donors and involved (fibrotic) skin of 7 patients with scleroderma were stimulated for 48 h with TNF-α (5 ng/ml) and levels of MMP-1 were quantitated by ELISA. The graph represents pooled results from 3 separate experiments in which 1-3 fibroblast lines from normal donors and patients with scleroderma were studied at the same time. Levels of MMP-1 (ng/ml) in supernatants of normal donor fibroblast cultures were compared by Student's t test to levels of MMP-1 in culture supernatants of scleroderma patients' fibroblasts.

The effects of TNF-α on the production of collagenase (MMP-1) protein were examined in dermal fibroblasts derived from normal donors and patients with scleroderma. A marked difference in both the constitutive and TNF-α-stimulated production of MMP-1 protein was observed (FIG. 7), with fibroblasts from patients with scleroderma producing significantly less constitutive and TNF-α-stimulated MMP-1 ($p<0.0005$ for each).

Production of MMP-1 was examined by ELISA as described below. Fibroblasts were harvested by trypsinization from stock cultures and added to wells of 24-well tissue culture plates (Corning Inc., Corning, N.Y.) at a plating density of $10^5$ cells per well in 500 µl of Complete EMEM. After 3 days culture, when cells were ≧80% confluent, the medium was changed to complete EMEM containing 5% FCS for 24 h, at which time medium was again changed to fresh Complete EMEM containing 5% FCS (450 µl per well). Stimulants such as human recombinant TNF-α (2.5 ng in 50 µl PBS containing 0.1% BSA) (R & D Systems, Minneapolis, Minn.), human recombinant IL-1β (125 pg in 50 µl PBS containing 0.1% BSA) (R & D Systems) or 50 µl PBS containing 0.1% BSA were each added to duplicate wells. Fibroblasts were cultured for 48 hours, after which culture supernatants were carefully removed and frozen at −80° until assayed for MMP-1 or TIMP-1 protein by ELISA. MMP-1 and TIMP-1 proteins secreted into the culture medium were measured by ELISA as previously described (Clark et al., 1985; Postlethwaite et al., 1988).

Figure 8A:
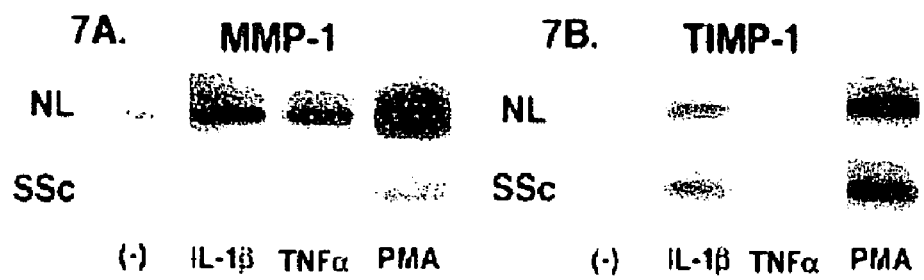
FIG. 8A shows impaired MMP-1 protein expression in fibroblasts explanted from involved skin of patients with scleroderma as determined by ELISA. Culture medium from duplicate wells were pooled and analyzed by ELISA for levels of MMP-1 and TIMP-1. Fibroblasts obtained from 5 healthy donors (NL) and 4 patients with scleroderma (SSc) were stimulated for 48 hr with IL-1β (250 pg/mL) or TNFα (5 ng/mL). The results are representative of three separate experiments in which these same cell lines were studied at the same time.
Figure 8B:
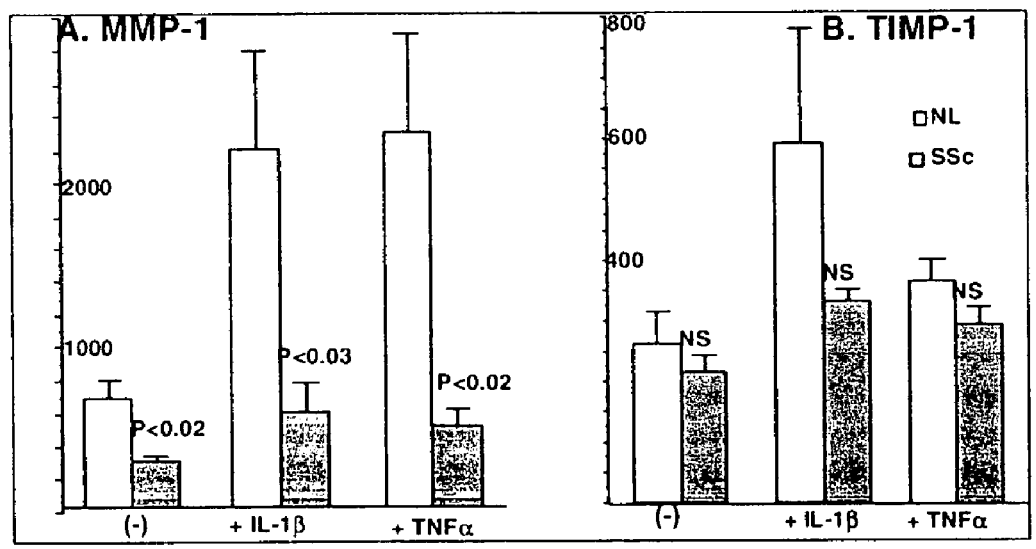
FIG. 8B shows impaired MMP-1 protein expression in fibroblasts explanted from involved skin of patients with scleroderma as determined by Western blot analysis. Fibroblasts from 1 randomly selected normal (NL) and 1 randomly selected patient with scleroderma (SSc) were cultured with or without IL-1β, TNF-α, or PMA for 48 hr in serum-free medium. Culture supernatants were analyzed on a 12.5% polyacrylamide gel and probed with polyclonal antibodies against MMP-1 and TIMP-1. The MMP-1 and TIMP-1 bands bound by respective specific antibodies were detected in a biotin-streptavidin-alkaline phosphatase color reaction.

As shown in FIG. 8, the MMP-1 protein levels in the culture supernatants 48 hours following stimulation with IL-1β or TNF-α were significantly reduced in fibroblasts derived from the skin of patients with scleroderma compared to fibroblasts derived from the skin of normal donors, as measured by ELISA (FIGS. 8A). However, the expression of TIMP-1 protein, a potent inhibitor of MMP-1, was not significantly different between fibroblasts derived from involved skin of patients with scleroderma and normal skin as measured by ELISA (FIG. 8A). Western blot performed on a randomly selected scleroderma and normal donor fibroblast lines confirmed the results obtained by ELISA (FIG. 8B).

Levels of MMP-1 mRNA was examined by semi-quantitative RT-PCR as described below. Total cellular RNA was isolated using Tri Reagent (Sigma Aldrich, St. Louis, Mo.). cDNA was synthesized from total RNA using reverse transcription reaction (RT) employing AMV reverse transcriptase and oligo $dT_{(18)}$ (Promega, Madison, Wis.). cDNA thus obtained was diluted 1:5 and 1:20 in sterile deionized water. Equal volumes of diluted and undiluted cDNA samples were amplified by polymerase chain reaction (PCR). The primer sequences are given in Table 1. PCR was run for 25, 28, 30, and 35 cycles using specific sets of primers.

The sense and antisense primer sequences and annealing temperatures used for various messages are presented in Table 1. The housekeeping enzyme gene GAPDH served as internal control to correct for possible variation of total RNA amount used in each message assay. The PCR products were run on a 2% agarose gel and stained with ethidium bromide. The gel bands obtained from optimal amplification (exponential phase) of each message were scanned, and the density was measured using an Alpha Innotech Imaging System (Foster City, Calif.). The values were expressed as ratios of specific message to that of the housekeeping genes, GAPDH or β-Actin.

Figure 9A:
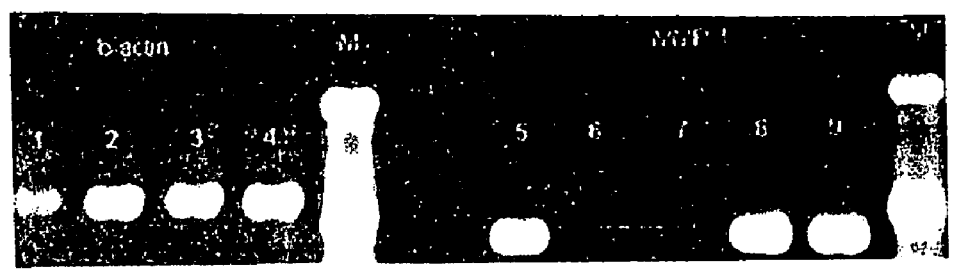
FIGS. 9A-B show impaired MMP-1 protein expression in fibroblasts explanted from involved skin of patients with scleroderma as determined by semi-quantitative RT-PCR. Skin fibroblasts were grown from biopsies from involved skin of patients with scleroderma (SSc). Within the first 5 or 8 passages, the fibroblasts were stimulated with IL-1β (100 pg/ml) and harvested within 8-12 h. Total RNA was extracted, reverse transcribed, and cDNA amplified using specific primers (Table 1). The PCR products were analyzed on a 2% agarose gel, stained with ethidium bromide, and photographed.
Figure 9B:
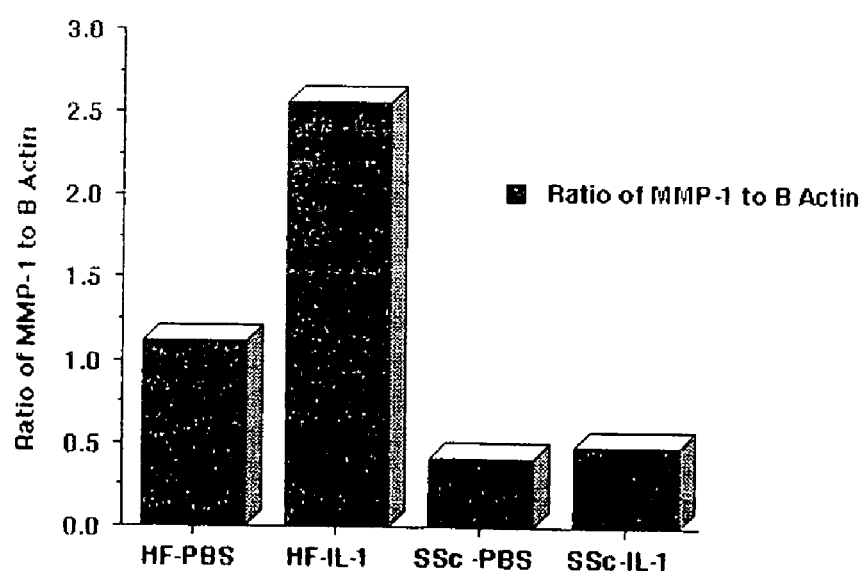

As shown in FIG. 9, in the presence or absence of IL-1b stimulation, very low expression of MMP-1 mRNA as determined by semi-quantitative RT-PCR was detected in fibroblasts derived from patients with scleroderma.

TABLE 1

Primer Sequences Used In Semi-Quantitative RT-PCR

| | | |
|---|---|---|
| GAPDH | Sense: GCAGGGGGAGCCAAAAGGG | (SEQ ID NO:1) |
| | Antisense: TGCCAGCCCCAGCGTCAAAG | (SEQ ID NO:2) |
| b-Actin | Sense: GTGGGCCGCCCCAGGCACCA | (SEQ ID NO:3) |
| | Antisense: CTCCTTAATGTCACGCACGAT | (SEQ ID NO:4) |
| icIL-ira type 1 | Sense: CCACCATGGCTTTAGAGACCATC | (SEQ ID NO:5) |
| | Antisense: CTACTCGTCCTCCTGGAAGTA | (SEQ ID NO:6) |
| sIL-ira | Sense: GAATGGAAATCTGCAGAGGCCTCCGC | (SEQ ID NO:7) |
| | Antisense: GTACTACTCGTCCTCCTGG | (SEQ ID NO:8) |
| MMP-1 | Sense: ACCTGAAGAATGATGGGAGGCAAGT | (SEQ ID NO:9) |
| | Antisense: CATCAAAATGAGCATCTCCTCCAATACCT | (SEQ ID NO:10) |
| TIMP-1 | Sense: AACCCACCATGGCCCCCTTTGAG | (SEQ ID NO: 11) |
| | Antisense: GTTCCACTCCGGGCAGGATTCAGG | (SEQ ID NO: 12) |

Additionally, the intracellular IL-1alpha protein and mRNA from fibroblasts derived from involved skin of four SSc patients was compared with dermal fibroblasts of four age-matched normal donors and an additional control of similar ($5^{th}$-$8^{th}$ passage). It was observed that unstimulated SSc fibroblasts contained significantly higher basal levels of IL-1 alpha protein than the controls. No IL-1 alpha was detected in the culture media. Although ELISAs do not distinguish between precursor and mature IL-1 alpha protein, it is contemplated that the intracellular IL-1 alpha was the precursor form.

Figure 10:
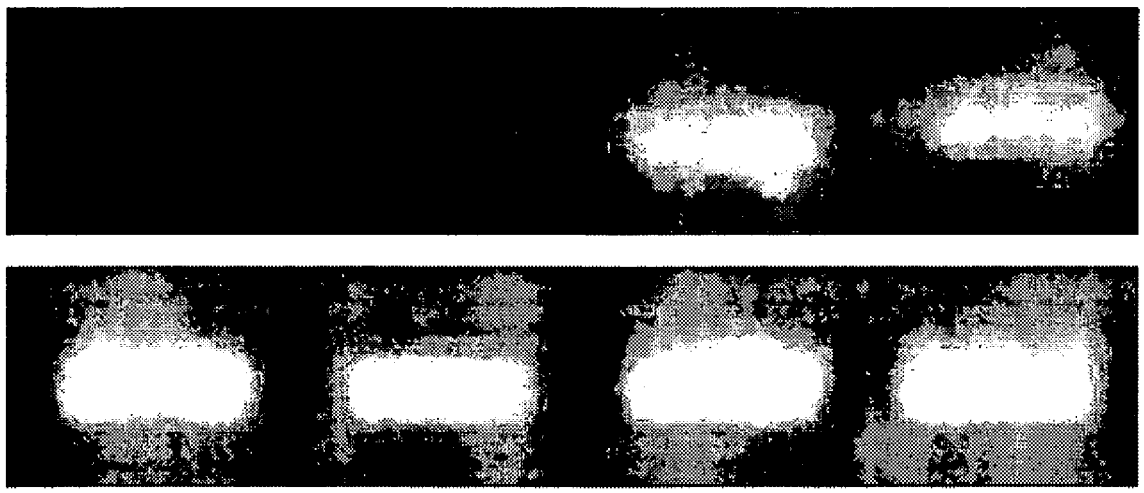
FIG. 10 shows expression of preIL-1 alpha mRNA in SSc fibroblasts compared to the normal fibroblasts. PCR products from reverse transcribed RNA from unstimulated fibroblasts of two SSc patients (lanes 3 and 4) and two matched controls (lanes 1 and 2) were run on agarose gel. Top panel: PCR with primers for IL-1 alpha. Bottom panel: PCR with primers for alpha-actin.

Further, the mRNA for preIL-1 alpha in the unstimulated normal and SSc fibroblasts were also compared. Total RNA was extracted and reverse transcribed and amplified by PCR using primers for IL-1 alpha and alpha-actin cDNA. As shown in FIG. 10, the results were in agreement with the ELISA result since fibroblasts from the four SSc patients produced higher levels of IL-1 alpha mRNA than those from three controls. Additionally, the fibroblasts from one control had basal IL-1 alpha mRNA compared to the SSc fibroblasts.

Figure 11B:
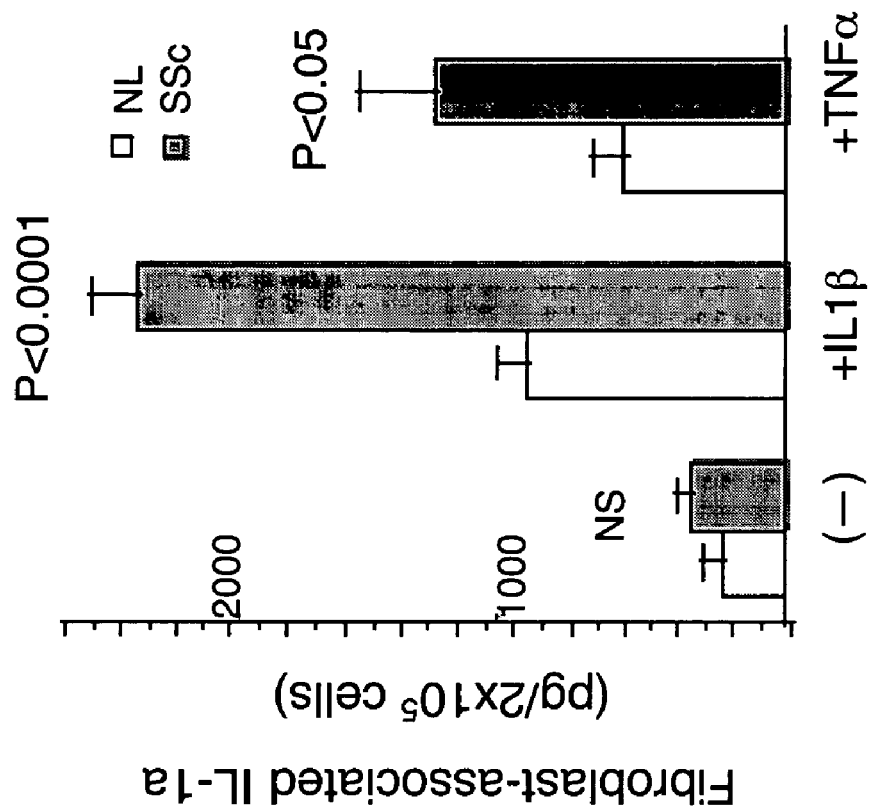
FIG. 11A-B show greater levels of cell-associated IL-1alpha and IL-1ra in the SSc fibroblasts than in the control after cytokine stimulation. Fibroblasts were grown to confluence and then cultured with or without 125 pg/ml IL-1 beta or 1 ng/ml F alpha in media containing 5% FCS for 48 hours. Cell layers were washed and disrupted by sonication. ELISAs for IL-1 alpha (FIG. 11A) and IL-1ra (FIG. 11B) were performed on the extract. Unstimulated cells (NS) are not represented in FIG. 11A since the cell associated IL-1 alpha in this number of unstimulated cells was below the limit of the assay.
Figure 11A:
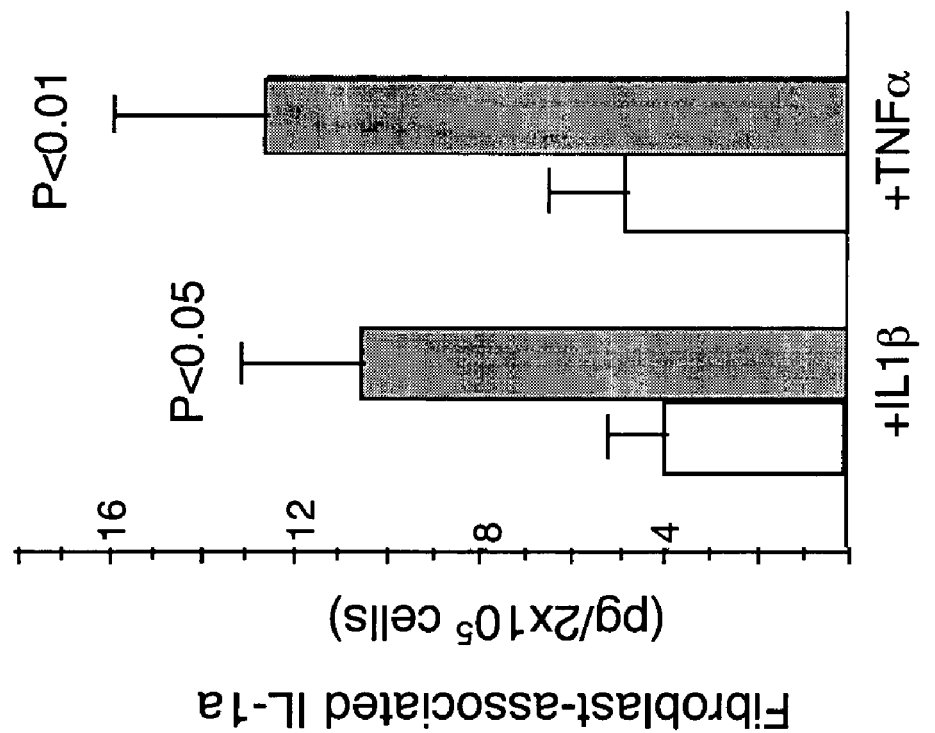

Since the relationship between IL-1 alpha and IL-1ra was not studied in fibroblasts, the levels of cell associated IL-1 alpha and IL-1ra in SSc and control fibroblasts before and after stimulation with IL-1 alpha or TNF alpha were measured. As shown in FIG. 11, there were substantially greater levels of cell-associated IL-1 alpha and IL-1ra in the SSc fibroblasts than in the controls after cytokine stimulation.

Figure 12A:
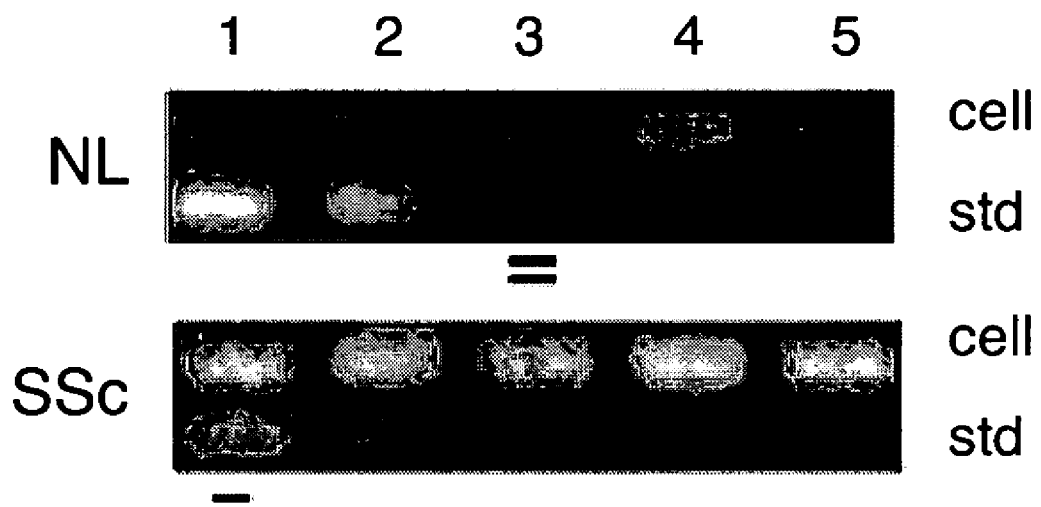
FIG. 12A-B show more mRNA for preIL-1 alpha and icIL-1ra in fibroblasts of patients with SSC than in stimulated controls. Total RNA, purified from fibroblasts treated with IL-1, was reverse transcribed. Input of this cDNA was normalized with I-actin. Competitive PCR was performed in presence of 5-fold dilutions of the appropriate internal standard (competitors) using primers for IL-L alpha or icIL-1ra. PCR products were analyzed by electrophoresis on 1% agarose gels. Results form one SSc patient and the matched control are shown. Lane 1: Highest concentration of standard ($2.4 \times 10^{14}$ M for IL-L alpha, $1 \times 10^{-15}$ M for icIL-1ra). Lane 5: Lowest concentration of standard. The size of the amplified fragment from the standard (<s) is smaller than that of the cell-derived cDNA (<c). The + below each panel designates the tube in which concentrations of target and competitor are nearest to equivalence.
Figure 12B:
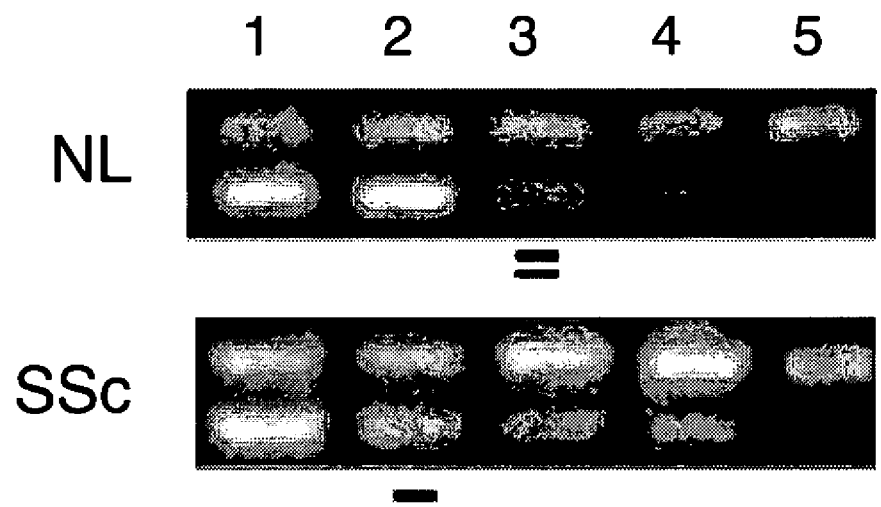

Next, the mRNA for preIL-1 alpha in IL-1beta-stimulated normal and SSc fibroblasts were measured by reverse transcription of total cellular RNA, followed by PCR amplification in presence of varying amounts of a synthetic competitor (internal standard) cDNA, which hybridizes to the same primers as the target (IL-1 alpha) sequence. Consistent with the results discussed above, it was observed that all four SSc patients had markedly more (15-fold) mRNA precursor for IL-1 alpha than four of the five stimulated controls. The control fibroblasts with elevated basal IL-1 alpha mRNA had as much induced IL-1 alpha mRNA as the SSc fibroblasts. A representative comparison between cells from one SSc patient and the matched normal is shown in FIG. 12.

The same technique was used to detect mRNA for IL-1ra in the same total preparation. Further, to distinguish between sIL-1ra and icIL-1Ra mRNA, specific 5' primers complementary to their different (alternatively spliced) 5' regions and a common 3' primer complementary to the shared sequence were used. Only the mRNA for icIL-1ra was detected in IL-1beta stimulated fibroblasts from three SSc patients and three normal controls. In one SSc and one normal sample, both icIL-1ra and sIL-1ra mRNA were detected but the sIL-1ra mRNA was barely detectable (not shown). Therefore, it was inferred that most of the cell associated IL-1ra was in the intracellular form. Additionally competitive PCR of CDNA using probes and internal standard for icIl-1ra was performed. Greater icIl-1ra mRNA was observed in stimulated SSc fibroblasts (15-fold) than normal fibroblasts consistent with the ELISA results. A representative comparison of cells from one SSC patient and the matched control is shown in FIG. 12.

Figure 13:
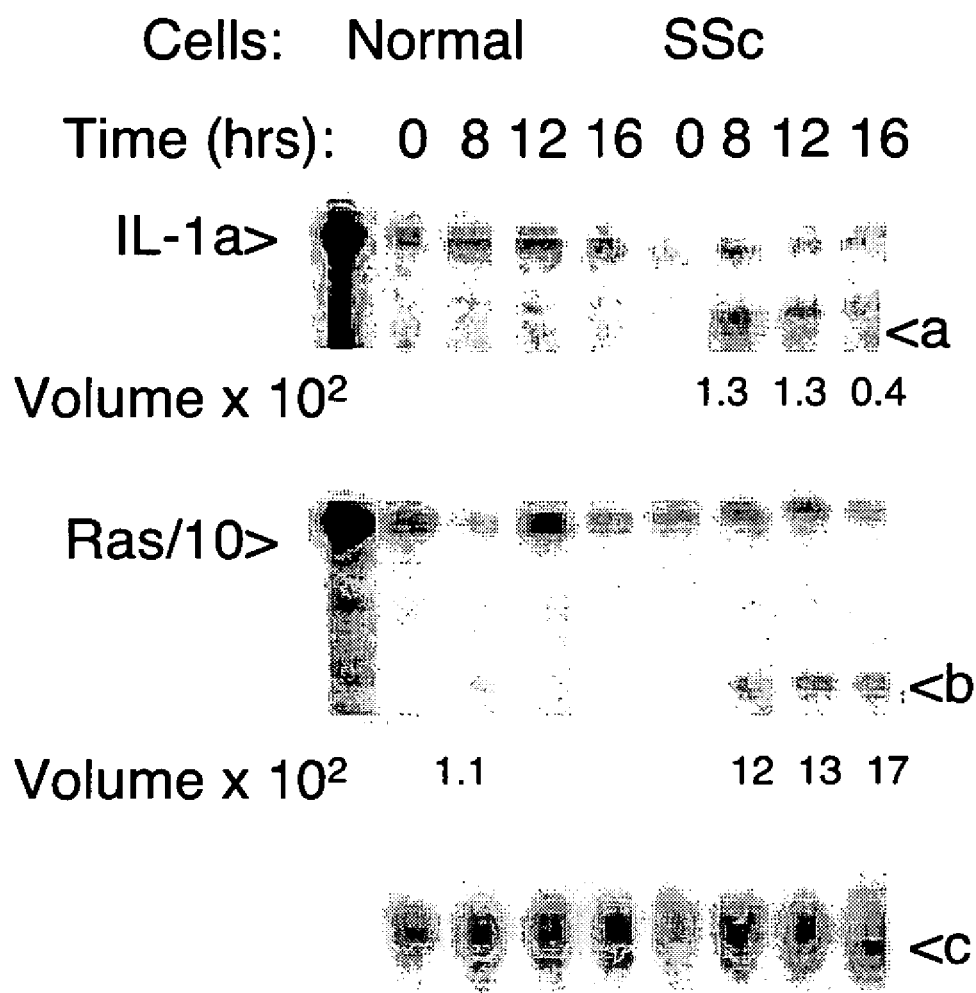
FIG. 13 shows the presence of IL-L alpha and icIL-1ra mRNA in the SSc fibroblasts at 8, 12 and 16 hours than in the controls by ribonuclease protection assay.

Further, ribonuclease protection assay (RPA) was used to compare mRNA levels and to study the time course of precursor IL-1 alpha and icIL-1ra production (FIG. 13). Replicate cultures of normal and SSc fibroblasts were treated with IL-1beta and harvested by trypsin treatment at various times after stimulation. Poly (A)+ RNA was hybridized to $^{32}$P-labeled riboprobes for IL-1I and G3PDH and to a riboprobe which is complementary to 216 bases of sIL-1ra and 160 bases of IcIl-1ra mRNA (probe IRAs/ic). Under the conditions of probe excess used for these assays, this probe protected both IL-1MRNAs, without loss of sensitivity when both mRNAs were mixed in various proportions (not shown). IL-1alpha and icIL-1ra mRNA were easily detected in SSc fibroblasts at 8, 12 and 16 hours in amounts greater than in the matched control line as indicated by the band volumes normalized to G3PDH. No IL-1alpha and icIL-1ra mRNA were detected at 0 hours, because this technique is less sensitive than PCR.

EXAMPLE 3

Cloning and Transfection of Intracellular Isoform of IL-1 Receptor Antagonist

Based on the above findings and previous observation that scleroderma fibroblasts have elevated intracellular isoform of IL-1 receptor antagonist (icIL-1ra), the relationship between the expression of the intracellular isoform of IL-1 receptor antagonist and MMP-1 was explored in cells transfected with plasmid encoding the intracellular IL-1 receptor antagonist. Cloning and transfection of intracellular isoform of IL-1 receptor antagonist are described below.

Poly(A)$^+$ RNA obtained from THP-1 monocytic cells (ATCC, Manassas, Va., USA) stimulated with 1 mg/ml LPS and 100 ng/ml PMA was reverse transcribed using oligo (dT)$_{18}$ primers and random hexamers. The cDNA thus obtained was subjected to polymerase chain reaction (PCR) using 5'- and 3'-primers corresponding to the coding sequence of icIL-1ra Type 1 sequence as reported by Haskill et al. (1991). Desired restriction enzyme sites were incorporated into the terminals of each primer for cloning.

The correct sequence of the cloned icIL-1ra Type 1 was verified by automated dye terminator cycle sequencing (ABI Prism Kit, Perkin Elmer, Foster City, Calif.) at the University of Tennessee Molecular Resource Center. The sequence of the cloned icIL-1ra corresponds to the isoform designated as icIL-1ra type 1. The cDNA for icIL-1ra type 1 was then cloned into an expression plasmid (pLXSN) carrying a neomycin resistance gene. The icIL-1ra type 1 cDNA was placed under the control of an SV40 promoter (pLXSN icIL-1ra). Unmodified plasmid carrying the neomycin resistance gene served as control (HF-VECTOR). Plasmids (pLXSN icIL-1ra type 1 and pLXSN-vector) were amplified in E. coli HB101/JM109 and purified using commercially available plasmid purification kit (Promega, Madison, Wis.).

Fibroblasts were transfected using LipofectAMINE™ 2000 Reagent obtained from Invitrogen Life Technologies following the manufacturer's protocol. Briefly, one day prior to transfection, 2×10$^5$ cells were seeded per well (in 500 μl) in a 24-well plate. The cells were maintained in Complete DMEM without antibiotics. About 1.0 μg of plasmid DNA was taken up in 50 μl of OPTI-MEM™ with reduced serum (Life Technologies Inc. Gaithersburg, Md.). For each well of cells to be transfected, 2 μl of LipofectAMINE™ reagent was added to 50 μl of OPTI-MEM™ and incubated at ambient temperature for 5 min. Diluted plasmid DNA was then combined with the diluted LipofectAMINE™ Reagent and incubated at ambient temperature for 20 min to allow DNA-LipofectAMINE™ complexes to form. The plasmid DNA-LipofectAMINE™ complex was then added to each well and mixed gently by rocking the plates back and forth. The cells were incubated at 37° C. for 4-6 h. To each well an additional 500 ul of OPTI-MEM™ with reduced serum was added, and the incubation was continued for another 48-72 h. The medium was then replaced with DMEM containing penicillin, streptomycin and 600 μg/ml of geneticin (Life Technologies Inc.). Cells were incubated for 5-7 d with removal of dead cells and replenishment with complete fresh DMEM containing 600 μg/ml geneticin. Several days later and after 3-4 subcultures, only cells resistant to geneticin (600 μg/ml) were maintained. Such stably transfected cells were tested for the expression of icIL-1ra by semi-quantitative RT-PCR and by ELISA.

Abundant levels of icIL-1ra type 1 mRNA levels were constitutively expressed in PLXSN-icIL-1ra-transfected normal human fibroblast (HF-icIL-1ra). The control fibroblasts transfected with PLXSN plasmid alone (HF-VECTOR) did not constitutively express detectable levels of the intracellular isoform of IL-1 receptor antagonist type 1 mRNA (FIG. 14). Upon stimulation with recombinant human (hr) IL-1β or hrTNF-α, the control cells expressed low levels of the intracellular isoform of IL-1 receptor antagonist type 1 mRNA (FIG. 14A). In contrast, fibroblasts transfected with PLXSN-icIL-1ra expressed significantly higher levels of intracellular isoform of IL-1 receptor antagonist type I protein compared to vector controls as measured by ELISA (FIG. 14B, p=0.005).

Further, to investigate a possible relationship between dysregulation of intracellular IL-1 alpha and icIL-1ra, and the disturbance of normal balance between MMP-1 and TIMP-1, normal fibroblasts (early passage infant foreskin fibroblasts) were transduced to constitutively produce precursor IL-1 alpha or icIL-1ra. As discussed above, the fibroblasts were transduced using the retroviral vector pLXSN containing the appropriate cDNA. Thus, the human dermal fibroblasts (HDF) so treated were designated as HDF-icIL-1ra (expressing icIL-1ra), HDF-preIL-1 alpha (expressing preIL-1 alpha), HDF-IL-1 alpha pro (expressing the propeptide region of the precursor IL-1 alpha) and HDF-vec (containing unmodified vector). Transduced and vector-controlled cells compared in each experiment were always derived from the same donor and passaged identically. Transduced cells and The HDF-vec controls exhibited normal morphology and growth characteristics.

Unstimulated transduced HDF were shown by RPA to constitutively produce abundant amounts of the appropriate retrovirally encoded mRNA transcripts (not shown). Synthesis of protein products was demonstrated by ELISA (Table 2). Increased constitutive production of icIL-1ra was observed in HDF-preIL-1 alpha. In distinct contrast, no increase in constitutive production of pre-IL1 alpha was observed in HDF-icIL-1ra.

TABLE 2

Basal cytokine levels in transduced fibroblasts.

| Fibroblasts | IL-1 alpha in | | IL-1ra in | |
|---|---|---|---|---|
| | Cells | Media | Cells | Media |
| HDF-vec | * | * | 158 ± 26 | # |
| HDF-I pro | * | * | 51 ± 5 | # |
| HDF-preIL-1 alpha | 12.7 ± 0.3 | * | 695 ± 49 | 11.0 ± 0.5 |
| HDF-icIL-1ra | * | * | 1495 ± 35 | 15.5 ± 0.7 |

Intracellular concentrations are expressed as pg/2 × 10$^5$ cells; media concentrations as pg/ml.
* below detection limit of 4 pg/ml.
below detection limit of 7.5 pg/ml.

Further, the synthesis of appropriate size protein product was demonstrated by biosynthetic labeling and immunoprecipitation as discussed in Higgins, et al., 1994 and using specific antibodies as shown in FIG. 15. The transduced cells, like SSc fibroblasts released no detectable IL-1 alpha into the culture media. It is therefore likely, that these cells do not process or secrete preIL-1alpha. However, HDF-icIL-1ra cells did release IL-1ra into the culture media. Stimulated cells usually released less than 100 pg/ml after 24 hours, but a maximum of 700 pg/ml was observed in one experiment.

Next, to test whether the normal fibroblasts transduced to constitutively make precursor IL-1alpha or TNF alpha show a response pattern similar to SSc fibroblasts, these transduced fibroblasts were stimulated with IL-1 beta or TNF alpha and the cell-associated IL-1ra was measured. Like the SSc fibroblasts, the HDF-preIL-1 alpha synthesized significantly more cell associated IL-1ra than the controls HDF-vec or HDF-IL-1 alpha pro in response to either of the cytokines. The peak IL-1ra production was at 24 hours (FIG. 16) and significant differences persisted for at least 48 hours. In dose response experiments, IL-1ra production was maximal after stimulation with 125 pg/ml IL-1beta and did not change with additional IL-1beta.

Further, to determine whether this cell-associated IL-1ra was the icIL-1ra or sIL-1ra, poly(A)+ RNA was isolated from HDF-vec and HDF-preIL-1 alpha stimulated with IL-1beta and probed for icIL-1ra and sIL-1ra by RPA. As shown in FIG. 16, icIL-1ra mRNA peaked at 8 hours in both HDF-vec and HDF-preIL-1ra. A more pronounced response was observed in HDF-preIL-1 alpha. mRNA for sIL-1ra was barely detectable. Therefore, most of the cell-associated IL-1ra in the HDF was likely to be the intracellular isoform. Additionally, it was also observed that the stability of icIL-1ra mRNA in IL-1I stimulated, actinomycin D-treated HDF-vec, HDF-alpha pro, and HDF-preIL-1 alpha was similar (half life=3 hrs). These suggested that the upregulation of icIl-1ra mRNA by preIL-1 alpha occurred at the level of transcription.

Since IL-1 alpha was not detected in the culture media of HDF-preIL-1 alpha, it seemed unlikely that extracellular IL-1 alpha was responsible for the upregulation of icIl-1ra in these cells. However, to test this possibility HDF-vec and HDF-preIL1 alpha were grown and stimulated with IL-1 alpha or IL-1 beta in the continuous presence of neutralizing anti-IL-1 antibody (20 ng/ml) and then assayed for cell-associated icIL-1ra (table 3). It was observed that neutralizing anti-IL-1 alpha antibodies had little effect on icIL-1ra production by HDF-preIL-1 alpha.

TABLE 3

Effect of anti-IL-1 on icIL-ra.

| Fibroblasts and treatment | IL-1ra (pg/2 × 10⁶ cells) | |
|---|---|---|
| | (−) IL-1 alpha | (+) IL-1 alpha |
| HDF-Vec | | |
| No antibody | 8 ± 3 | 636 ± 20 |
| HDF-preIL-1 alpha | | |
| No antibody | 737 ± 41 | 2469 ± 233 |
| Anti-IL-1 alpha | 608 ± 8 | 2283 ± 390 |
| Anti-IL-1ra | 600 ± 45 | 2339 ± 41 |
| Anti-IL-1 alpha + Anti-IL-1ra | 679 ± 29 | 2757 ± 70 |

Further, whether the constitutive expression of precursor of IL-1 alpha or icIL-1ra would alter the production of other cytokines produced in response to IL-1 beta or TNF alpha was investigated by ELISA. Control and transduced fibroblasts were treated with IL-1 beta and culture media was tested for production of GMCSF, IL-6 and MCP-1. As shown in Table 4, HDF-preIL-1 alpha produced greater basal MCP-1 and IL-6, but after cytokine stimulation the amounts were not different. Similar results were obtained after TNF alpha stimulation. Next, whether IL-6 was involved in upregulation of icIL-1ra was investigated by treating HDF-preIL-1 alpha with neutralizing anti-IL-6 antibodies before and during stimulation with IL-1 beta. No effect of anti-IL6 was observed.

TABLE 4

Cytokine production by transduced cells.

| | | Cytokines in culture media (pg/ml) | | |
|---|---|---|---|---|
| Cells | Treatment | GMCSF | IL-6 | MCP-1 |
| HDF-vec | (−) | 4 | 248 | 2300 |
| | IL-1beta | 1520 | 1580 | 17,000 |
| | TNF alpha | 1128 | 1590 | 15,200 |
| HDF-preIL-1I | (−) | 24 | 2,800 | 9,700 |
| | IL-1beta | 1960 | 8710 | 15,200 |
| | TNF alpha | 720 | 8,650 | 8,700 |
| HDF-icIL-1ra | (−) | 2 | 180 | 2,150 |
| | IL-1beta | 2,240 | 1580 | 16,200 |
| | TNF alpha | 680 | 1595 | 16,240 |

Additionally, TGF alpha production was also measured by ELISA and no difference was observed between HDF-vec and HDF-preIL-1I either before or after IL-1I stimulation. Hence, based in the measurement of the various cytokines it was concluded that transduction of fibroblasts to constitutively produce precursor IL-1I does not result in global alteration of responses to IL-1I or TN F alpha stimulation. Rather specific differences are observed depending on the expressed protein.

Next, the MMP-1 production in the fibroblasts expressing increased intracellular pre-IL-1I and icIL-1ra was examined by incubating the cells in IL-1 and TNF alpha. HDF-preIL-1 alpha cells exhibited lower induction of MMP-1by IL-1beta than HDF-vec (FIG. 17) and thus resembled the SSc in this regard. However, unlike SSc, the basal and cytokine-stimulated levels of TIMP-1 were elevated in HDF-preIL-1 alpha as compared to HDF-vec. Since HDF-preIL-1 alpha cells make increased icIL-1ra after IL-1 beta/TNF alpha stimulation, whether cells constitutively producing icIL-1ra but not IL-1 alpha would behave the same way was examined. It was observed that after stimulation with IL-1beta or TNF alpha, HDF-icIL-1ra responded similarly to HDF-preIL-1 alpha; i.e MMP-1 induction was impaired but TIMP-1 was still induced (FIG. 18).

The ability of IL-1ra peptides to compete with [$^{125}$I] IL-1beta for binding to type I IL-1Rs on EL46.1 cells and their ability to block IL-1beta induction of ICAM-1 expression on fibroblasts and on IL-1 stimulation of collagenase and PGE$_2$ synthesis in infant foreskin fibroblasts was examined. Peptides that represented processed/mature form of human sIL-1ra were synthesized (Table 5).

TABLE 5

IL-1ra peptides synthesized.

| IL-1ra Peptide | Sequence | SEQ ID No. |
|---|---|---|
| 1-35 | RPSGRKSSKMQAFRIWDVNQKTFYLRNNQLVAGYL | 13 |
| 36-59 | QGPNVNLEEKIDVVPIEPHALFLG | 14 |
| 60-90 | IHGGKMCLSCVKSGDETRLQLEAVNITDLSE | 15 |
| 91-123 | NRKQDKRFAFIRSDSGPTTSFESAACPGWFLCT | 16 |
| 124-152 | AMEADQPVSLTNMPDEGVMVTKFYFQEDE | 17 |

None of the peptides were able to displace [$^{125}$I] IL-1beta from type I IL-1Rs on the EL46.1 cells (FIG. 19). Additionally a competitive binding assay was performed in which the IL-1ra peptides were added to the EL4 cells at the same time

[¹²⁵I] was added. No displacement of [¹²⁵I] IL-1 beta was observed from its receptors in the presence of these IL-1ra peptides. In contrast, greater than 90% displacement of [¹²⁵I] from EL4 cells was observed in the presence of a 100× excess of shrIL-1ra. These results indicated that if any of these peptides bind to type IL-1Rs, they do so with affinities too low to be detected by competitive binding analysis.

Additionally, the ability of these peptides to inhibit IL-1 stimulated fibroblast functions (synthesis of collagenase and PGE$_2$ and expression of ICAM-1) known to be inhibited by IL-1ra were examined. It was observed that the amino terminal IL-1ra peptide, 1-35 (SEQ ID NO. 13), consistently inhibited IL-1-induced collagenase synthesis by dermal fibroblasts (FIG. 20) and different IL-1ra peptide, 60-90 (SEQ ID NO. 15), located in the middle of the molecule, inhibited IL-1-induced fibroblast synthesis of PGE2 (FIG. 21) and fibroblast surface expression of ICAM-1.

The observation that these peptides affected cell metabolism without binding to surface receptors suggested an intracellular mode of action. To potentially enhance translocation of the peptide, a nuclear localization sequence was added to the peptide. Table 6 shows pronounced effect of NLS-IL-1ra peptide on the TNF alpha and b-FGF-stimulated fibroblast collagenase production.

TABLE 6

Effect of NLS-IL-1RA6 peptide on TNF1 and b-FGF-stimulated fibroblast collagenase production.

| Treatment | Collagenase (ng/mL) |
|---|---|
| TNF alpha (5 ng/ml) + PBS | 9391 |
| TNF alpha (5 ng/ml) + NLS-IL-1RA6 (1 µg/ml) | 849 |
| TNF alpha (5 ng/ml) + NLS-IL-1RA6 (100 ng/ml) | 1254 |
| TNF alpha (5 ng/ml) + NLS-IL-1RA6 (10 ng/ml) | 1199 |
| TNF alpha (5 ng/ml) + NLS-IL-1RA6 (1 ng/ml) | 238 |
| TNF alpha (5 ng/ml) + NLS-IL-1RA6 (100 pg/ml) | 243 |
| TNF alpha (5 ng/ml) + hr SIL-IL-1RA6 (200 ng/ml) | 2819 |
| TNF alpha (5 ng/ml) + hr NLS-IL-1RA6 (200 ng/ml) | 3253 |
| bFGF (5 ng/mL) + PBS | 5058 |
| bFGF (5 ng/ml) + NLS-IL-1RA6 (1 µg/ml) | 5649 |
| bFGF (5 ng/ml) + NLS-IL-1RA6 (100 ng/ml) | 3199 |
| bFGF (5 ng/ml) + NLS-IL-1RA6 (10 ng/ml) | 3167 |
| bFGF (5 ng/ml) + NLS-IL-1RA6 (1 ng/ml) | 2541 |
| bFGF (5 ng/ml) + NLS-IL-1RA6 (100 pg/ml) | 2367 |
| PBS | 645 |

IL-1RA6 (1–35) = RPSGRKSSKMQAFRIWDVNQKTFYLRN-NQLVAGYL (SEQ ID No. 13)
NLS-IL-1RA6 =
KKKMEKRRPSGRKSSKMQAFRIWDVNQKTFYLRNNQLVAGYL (SEQ ID No. 18).
SIL-1RA = recombinant IL-1ra,
NLS-SIL-1RA = recombinant IL-1ra plus a nuclear localization sequence.

Next, due to the above-discussed observation smaller fragments as shown in table 7 at various dilutions were used to analyze the effect on IL-1-stimulated fibroblast collagenase production.

TABLE 7

IL-1ra (IL-1RA) synthetic peptides

| IL-1RA Peptide | Sequence | SEQ ID No. |
|---|---|---|
| IL-1RA-6 (1-35) | RPSGRKSSKMQAFRIWDVNQKTFYLRNNQLVAGYL | 13 |
| IL-1RA6-1 | RPSGRKSSKMQAIFRI | 19 |
| IL-1RA6-2 | MQAFRIWDVNQKTFYLR | 20 |
| IL-1RA6-3 | FYLRNNQLVAGYL | 21 |
| IL-1RA6-3A | FYLRNNQ | 22 |
| IL-1RA6-3B | NNQLVAGY | 23 |
| IL-1-RA6-3C | LVAGYLQG | 24 |

When different concentrations of these peptides (10 µg/mL, 1 µg/mL, 100 ng/mL) were used with IL-1 beta (100 pg/mL), it was observed that IL-1RA6-3B (SEQ ID No. 23, 1 µg/mL, 100 ng/mL) and IL-1RA6-3C (SEQ ID No. 24, 10 µg/mL, 1 µg/mL) inhibited IL-1-stimulated collagenase production.

Thus, it was found that SSc dermal fibroblasts expressed higher basal levels of preIL-1 alpha and higher stimulated levels of preIL-1 alpha and icIL-1ra, than the normal dermal fibroblasts. The SSc fibroblasts had blunted MMP-1 production in response to IL-1 beta and TNF alpha. When normal dermal fibroblasts were transduced to constitutively express intracellular preIL-1 alpha, they behaved like SSc fibroblasts and produced higher stimulated levels of icIL-1ra than control fibroblasts. Similarly, normal fibroblasts were also transduced to constitutively express icIL-1ra. These cells also behaved line SSc fibroblasts with impaired production of MMP-1 after cytokine stimulation. Thus, these cells could be used as models for studying disease-related alteration son cytokine response. Hence, excess levels of preIL-1 alpha causes overproduction of icIL-1ra in response to inflammatory mediators, which in turn contribute to impairs matrix degradation by blunting MMP-1 induction.

EXAMPLE 4

Expression of Collagenase (MMP-1) In Human Fibroblasts Transfected With Intracellular Isoform of IL-1 Receptor Antagonist In order to understand the relationship between intracellular isoform of IL-1 receptor antagonist (icIL-1ra type 1) and MMP-1 expression, human fibroblasts transfected with icIL-1ra type1 or vector alone were stimulated with hrIL-1β (100 pg/ml or 1.0 ng/ml) or hrTNF-α (5 ng/ml or 15 ng/ml). The MMP-1 mRNA levels were analyzed by semi-quantitative RT-PCR and real time RT-PCR.

Two-step real time RT-PCR analysis was performed by a fluorogenic 5' nuclease assay using TaqMan PCR reagents obtained from Applied Biosystems (Foster City, Calif.). The following primers were used to amplify MMP-1: Forward Primer, 5' GGCTTGAAGCTGCTTACGAATTT 3' (Seq ID No. 25); Reverse Primer, 5' GAAGCCAAAGGAGCTGTA-GATGTC 3'(SEQ ID No. 26). The dye-tagged MMP-1 specific probe (6FAM-TCCCTTTGAAAAACC GGACT-TCATCTCTG-TAMRA) (SEQ ID No. 27) was prepared by Applied Biosystem. The reactions were performed according to manufacture's protocol. Each sample was assayed in duplicate. The housekeeping gene GAPDH was used as a control to normalize the amount of RNA present in various test samples. The following primers obtained from Applied Biosystem were used to estimate GAPDH level in the samples: Forward primer 5' GAAGGTGAAGGTCGGAGT 3' (SEQ ID No. 28), Reverse primer 5' GAAATCCCATCA CCATCTTC 3'(SEQ ID No. 29), JOE-Labeled probe 5' CCGACTCTTGCCCT-TCGAAC 3'(SEQ ID No. 30). The relative value of MMP-1 in each sample was expressed as a ratio of the CT values of MMP-1 to that of corresponding GAPDH.

Results presented in FIG. 22A (semi-quantitative RT-PCR) and FIG. 22B (real time RT-PCR) show a significant decrease in MMP-1 mRNA levels in intracellular isoform of IL-1 receptor antagonist type 1 transfected fibroblasts compared to the controls (HF-VECTOR). The p values were 0.014, 0.002 and 0.031 for differences between HF-VECTOR and HF-icIL-1ra (unstimulated); HE-VECTOR and HF-icIL-1ra (IL-1-β treated) and HF-VECTOR and HF-icIL-1ra (TNF-treated), respectively.

Matrix metalloproteinase-1 mRNA levels were also measured by ribonuclease protection assay as follows. Fibroblasts maintained as described above were harvested 12-16 hours following exposure to hrIL-1β or hrTNF-α. Total cellular RNA was isolated as described above. Human matrix metalloproteinase multi-probe set (Cat # 551274) from BD Biosciences (Pharmingen, San Diego, Calif.) was used to quantitate the mRNAs. Synthetic anti-sense RNA was prepared using the BD RiboQuant™ in vitro transcription kit. Labeled probes for housekeeping genes (GAPDH and L32) were transcribed from respective linearized plasmids using T7 RNA polymerase in presence of $\alpha^{32}$P-UTP (BD RiboQuant™ Ribonuclease Protection Assay (RPA) Systems, BD Biosciences/Pharmingen, San Diego, Calif.). After overnight hybridization and digestion using RNase provided by the RiboQuant™ RPA kit, protected probes were resolved by PAGE on urea-acrylamide gels. The bands were visualized, and the intensities of the bands were quantified using a Bio-Rad Model GS-505 phosphor imager (Bio-Rad, Herculis, Calif.). The results are expressed after normalizing the intensities of MMP-1 bands from various samples to that of the housekeeping genes in respective samples.

Results from ribonuclease protection assay depicted in FIG. 22C show reduced expression of matrix metalloproteinase-1 mRNA in cells transfected with the intracellular isoform of IL-1 receptor antagonist type 1 (HF-icIL-1ra) compared to controls (HF-VECTOR). MMP-1 expression was also examined in cultures of HF-icIL-1ra and HF-VECTOR after stimulation with phorbol myristate acetate (PMA, 10 ng/ml). The results from two separate experiments presented in FIG. 23 show up to 50% reduction in MMP-1 mRNA levels in HF-icIL-1ra after PMA stimulation compared to HF-VECTOR.

In addition to matrix metalloproteinase-1 mRNA levels, matrix metalloproteinase-1 protein was also measured. Supernatants from HF-VECTOR and HF-icIL-1ra cells were collected after stimulation with hrIL-1β (100 pg/ml or 1 ng/ml), or hrTNF-a (5 ng/ml) for 48 h. MMP-1 protein levels in culture supernatants were determined by ELISA. Results from two separate experiments presented in FIG. 24 show significantly reduced levels of collagenase in HF-icIL-1ra compared to HF-VECTOR. These results show that human fibroblasts over-expressing the intracellular isoform of IL-1 receptor antagonist type 1 are refractory to matrix metalloproteinase-1 upregulation when exposed to potent stimulators such as IL-1β, TNF-α, or PMA.

EXAMPLE 5

Effect of Antisense Intracellular Isoform of IL-1R Antagonist On MMP-1 Expression To further study the direct relationship between intracellular isoform of IL-1 receptor antagonist (icIL-1ra type 1) and matrix metalloproteinase-1 expression, an antisense oligonucleotide against the sense mRNA of the intracellular isoform of IL-1 receptor antagonist type 1 was designed to specifically inhibit the translation of the intracellular isoform of IL-1 receptor antagonist type 1 into corresponding protein. Cells transfected with intracellular isoform of IL-1 receptor antagonist type 1 (HF-icIL-1ra) were treated with varying concentrations of antisense oligonucleotide directed against the intracellular isoform of IL-1 receptor antagonist type 1 mRNA. Oligonucleotide with a scrambled sequence was used as control. Both oligonucleotides were mixed with LipofectAMINE™ reagent to enhance cellular uptake.

Results presented in FIG. 25 show that HF-icIL-1ra treated with 300 mM antisense intracellular isoform of IL-1 receptor antagonist type 1 oligonucleotide expressed significantly higher levels of MMP-1 mRNA (p=0.001) compared to the controls (i.e. HF-icIL-1ra treated with PBS, with empty liposome, and oligonucleotide with scrambled sequence). These results show a direct relationship between increased intracellular isoform of IL-1 receptor antagonist type 1 and reduced MMP-1 expression in fibroblasts stimulated by agents such as IL-1β, TNF-a and PMA that normally upregulate MMP-1.

EXAMPLE 6

Expression of icIL-1ra In Transfected Fibroblasts and Phenotypic Features of Dermal Fibroblasts Overexpressing icIL-1ra Since it was observed that Ssc fibroblasts over-expressed icIL-ra type I when stimulated with cytokines, the effects of icIL-1ra type 1 in normal fibroblasts with regard to their phenotype and expression of MMP-1, α-SMA, as well as the expression of plasminogen activator inhibitor (PAI) that has been reported to be elevated in myofibroblasts was assessed.

The icIL-1ra type 1 CDNA insert was prepared as described earlier (Example 3). Dermal fibroblasts were obtained from infant foreskins by conventional explant culture techniques and grown in Dulbecco's modified minimal essential medium (DMEM) containing HEPES buffer, non-essential amino acids (NEAA), sodium pyruvate, 100 mM L-glutamine, 100 units/ml penicillin, 100 μg/m streptomycin and 9% fetal bovine serum (FBS) hereafter referred to as "complete DMEM". Low passage ($5^{th}$ to $10^{th}$) fibroblasts were used for transfection. The transfection was carried out using LipofectAMINE 2000 Reagent as described earlier (Example 3).

Levels of icIL-1ra Type 1 mRNA and ic-IL-1ra protein were assessed in HF-icIL-1ra and HF-Vector fibroblasts. Real-time RT-PCR was used to estimate the mRNA levels. Briefly, total cellular RNA was isolated from cells using Tri-Reagent (Sigma) followed by chloroform extraction and isopropanol precipitation. Total RNA was used for oligo dT mediated reverse transcription of messenger RNA species in each sample. Specific messages were amplified and detected by real-time PCR performed using the SYBR Green method (Applied Biosystems, Foster City, Calif.) using specific sets of forward and reverse primers (Table 8) in addition to the primers that are presented in Table 1.

TABLE 8

Primer sequences used to amplify specific cDNAs*

| | | |
|---|---|---|
| α-SMA | Sense: GTC CCC ATC TAT GAG GGC TAT | (SEQ ID NO. 31) |
| | Antisense: GCA TTT GCG GTG GAC AAT GGA | (SEQ ID NO. 32) |
| PAI | Sense: AAG GAC CGC AAC GTG GTT TTC TCA | (SEQ ID NO. 33) |
| | Antisense: TGA AGA AGT GGG GCA TGA AGC C | (SEQ ID NO. 34) |
| c-fos | Sense: AGC TGC ACT ACC TAT ACG TCT T | (SEQ ID NO. 35) |
| | Antisense: TCA AGT CCT TGA GGT CCA CAG | (SEQ ID NO. 36) |
| c-jun | Sense: GTC ATG AAC CAC GTT AAC GTG | (SEQ ID NO. 37) |
| | Antisense: TCC ATG CAG TTC TTG TCA ATG | (SEQ ID NO. 38) |
| Jun B | Sense: AGC TCA AGC AGA AGG TCA TGA | (SEQ ID NO. 39) |
| | Antisense: ATG TAA ACC TCG AGG TGG AAG | (SEQ ID NO. 40). |

The reactions were performed according to the manufacturer's protocol. Each sample was assayed in duplicate. The PCR product was detected by measuring the increase in fluorescence caused by binding of the SYBR Green dye to double-stranded DNA. The specificity of the product was confirmed by the generation of a specific melting/dissociation cure for each product. The housekeeping gene GAPDH was used as a control to normalize for the amount of RNA present in various test samples. The relative value of specific sample was expressed as a reciprocal ratio of the Ct values of each message to that of corresponding GAPDH.

The total intracellular IL-1ra type 1 protein was measured by ELISA (R&D systems, Minneapolis, Minn.). The transfected cells were harvested, washed once in serum-free DMEM, counted manually in a hemocytometer and lysed by incubation for 30 min at 4° C. with 50 mM Tris, 0.1% [(3-cholamidopropyl)dimethylammonio]-1-proanesulfonate (Sigma Aldrich Chemicals, St. Louis, Mo.), 0.1% Nonidet P-40 pH 7.5, containing protease inhibitors (25 mM benzamidine, 1 mM PMSF, 10 mM N-ethylmaleimide, 1 mMEDTA, 1.0 μg/ml leupeptin, 1.0 μg/ml aprotinin, and 1.0 μg/ml pepstatin). The cell lysates were cleared by centrifugation at 18, 000× g for 30 min at 4° C. Cleared lysates were stored at −80° until tested after adding 0.1 volumes of NaCl (to a final concentration of 0.9%) to each sample. The concentration of total icIL-1ra was expressed as ng/1×10$^6$ vector transfected (HF-vector) or icIL-1ra-transfected (HF-icIL-1ra) cells.

It was observed that abundant levels of icIL-1ra type 1 mRNA levels were constitutively expressed in PLXSN-icIL-1ra transfected fibroblast (HF-icIL-1ra). The control fibroblasts transfected with PLXSN plasmid alone (HF-VECTOR) did not constitutively express detectable levels of icIL-1ra type 1 mRNA (FIG. 26A). However, upon stimulation with hrIL-1β or hrTNF-α, the control cells did express low levels of icIL-1ra type 1 mRNA (FIG. 26A). Fibroblasts transfected with PLXSN-icIL-1ra expressed high levels of icIL-1ra protein compared to vector controls (FIG. 26B).

It has been reported that fibroblast that constitute fibrotic lesions of scleroderma are predominantly of the myofibroblast phenotype with characteristic morphology and increased α-SMA and PAI. Therefore, whether such features were characteristic of fibroblasts overexpressing icIL-1ra were also determined. Fibroblasts transfected with icIL-1ra or control plasmid were maintained in culture with complete DMEM for 6 week with medium change every 5$^{th}$ day. The myofibroblast phenotype was assessed by light microscopy, immunoperoxidase staining for α-SMA and mRNA levels of α-SMA and plasminogen activator inhibitor (PAI) was estimated by Sybrgreen real-time RT-PCR by using the primers listed in Table 8.

For immunoperoxidase staining, HF-Vector and HF-icIL-1ra fibroblasts were grown to subconfluency in 48-well flat bottom tissue culture plates. Medium was removed and cell layers were incubated with Cytofix/Cytoperm for 20 min and then with 0.3% hydrogen peroxidase (Sigma) for 5 min. Cell layers were then washed three times with Perm Wash. A 1:25 dilution of Sigma's mouse anti-human α-SMA clone 1A4 monoclonal antibody was added to the cell monolayers for 30 min and then washed three times with PermWash. Cell monolayers were then incubated with biotinylated rat anti-mouse IgG (Fab-specific) for 30 min and washed three times with Perm Wash. Streptavidin-Horseradish peroxidase was then added to the cell layers for 10 min and then washed 3 times with Perm Wash. Substrate AEC (BD Pharmingen) or DBA was added to the cell monolayers for 10 min, washed with distilled water, counterstained with 0.02% Coomassie Blue for 20 min and finally washed three times with distilled water.

It was observed that fibroblasts transfected with plasmid alone retained a spindle shaped morphology (FIG. 27A) with little staining for α-SMA (FIGS. 27C, 27E). In distinct contrast, fibroblasts over-expressing icIL-1ra assumed a myofibroblast-like appearance (FIG. 27B) and stained for α-SMA (FIGS. 27D, 27F). Real time PCR analysis of constitutive mRNA expression of the myofibroblast marker, α-SMA showed a significantly enhanced expression of icIL-1ra overexpressing fibroblasts compared to control fibroblasts transfected with plasmid alone (p=0.002) (FIG. 28).

Since it was reported that differential regulation of PAI-1 gene expression in human fibroblasts predispose to a fibrotic phenotype (Huggins, P. J. et al., 1999), the possible association between icIL-1ra and expression of PAI mRNA was determined by examining fibroblasts over-expressing icIL-1ra by real-time RT-PCR. It was observed that fibroblasts over-expressing icIL-1ra type 1 (HF-icIL-1ra) had increased constitutive levels (p=0.02) of PAI mRNA compared to controls (HF-Vector) (FIG. 29).

EXAMPLE 7

Expression of MMP-1 in icIL-1ra Type 1 Transfected Fibroblasts Exposed to IL-1β or TNF-α or PMA To determine the impact of over-expression of icIL-1ra type 1 on MMP-1 expression, human fibroblasts transfected with icIL-1ra type 1 or vector alone were stimulated with hr-IL-1β, hrTNF-α and PMA. Briefly, transfected fibroblasts were continuously maintained in complete DMEM containing 600 μg/ml Geneticin. These fibroblasts were harvested from confluent monolayers by trypsin treatment. Equal numbers of fibroblasts/well were seeded in 12-well or 24-well plates and grown to confluence for 72 hrs. One day prior to treatment with hrIL-1β, hrTNF-α or PMA, the initial growth medium was replaced with complete DMEM containing 5% FBS. Separate plates were set up for mRNA and protein analysis. Duplicate wells were set up for each assay condition. Fibroblasts were then exposed to 1.0 ng/ml hrIL-1β, 5 or 10 ng/ml hrTNF or 10 ng/ml of PMA. The fibroblasts were harvested 12-16 h after treatment for mRNA analysis. One ml of tri-Reagent was added to each well to lyse the fibroblasts. The cell lysates thus obtained were stored at −80° C. until analyzed.

It was observed that fibroblasts over-expressing icIL-1ra (HF-icIL-1ra) exhibited a significant decrease in MMP-1 mRNA levels compared to the controls (HF-VECTOR) (FIG. 30). Additionally, the results from two separate experiments showed up to 50% reduction in MMP-1 mRNA levels in HF-icIL-1ra after PMA stimulation compared to HF-Vector (data not shown).

ELISA measured MMP-1 protein secreted into culture medium. Briefly, culture supernatants were collected 48 h after treatment with hrIL-1β (1.0 nag/ml), hrTNF-α (5 ng/ml) and cleared by centrifugation at 18,000×g for 30 min at 4° C. Cleared supernatants were treated with protease inhibitors (25 mM benzamidine, 1 mM PMSF, 10 mM N-ethylmaleimide, 1 mM EDTA, 1.0 μg/ml leupeptin, 1.0 μg/ml aprotinin and 1.0 μg/ml pepstatin) and the level of MMP-1 protein was determined. Results from two separate experiments showed significantly reduced levels of collagenase in HF-icIL-1ra compared to HF-VECTOR (FIG. 31). The results showed that human fibroblasts over-expressing expressing icIL-1ra type 1 were refractory MMP-1 upregulation when exposed to potent stimulators such as IL-1β, TNF-α or PMA.

EXAMPLE 8

Specificity of icIL-1ra Type 1 Action On MMP-1 Expression

Using the approach described in Example 5, a phosphorothioate-derivatized antisense oligodeoxynucleotide complimentary to −6 to +12 (5'-CGTCTGTAAAGGCATGGG-3' SEQ ID NO. 41) of the natural icIL-1ra type 1 was synthesized and RHPLC purified. This antisense oligonucleotide against the sense mRNA of icIL-1ra type 1 was designed to specifically inhibit the translation of icIL-1ra type 1 into corresponding protein and to study the direct relationship between icIL-1ra type 1 and MMP-1 expression. Similarly, an antisense oligonucleotide with scrambled sequence was prepared and used as control. Fibroblasts overexpressing icIL-1ra type 1 were transfected with 50 mM, 100 mM and 300 mM of icIL-1ra type 1 antisense oligonucleotide (24 h prior to stimulation with 1.0 ng/ml of hrIL-1β) using the LipofectAMINE protocol. The fibroblasts were harvested for RNA extraction 12-18h after stimulation. It was observed that HF-icIL-1ra treated with 200 mM antisense icIL-1ra type 1 oligonucleotide expressed significantly higher levels of MMP-1 mRNA compared to the controls (i.e. HF-icIL-1ra treated with PBS, with empty liposome and the oligonucleotide with the scrambled sequence) (FIG. 32). The results indicated a direct association between increased icIL-1ra type 1 and decreased MMP-1 expression in fibroblasts stimulated by agents such as IL-1β, TNF-α and PMA that normally regulate MMP-1.

EXAMPLE 9

AP-1 Transcription Factors Components c-jun and c-fos

In fibroblasts, c-fos, c-jun and Jun B are involved in the transcription of MMP-1 (Hall, M. C. et al., 2003; Sugioka, Y. et al., 2004; Chakraborti, S. et al., 2003). In icIL-1ra transfected fibroblasts, there was reduced expression of MMP-1 mRNA and protein that was reversed by transfection of HF-icIL-1ra with antisense oligonucleotides directed against icIL-1ra (FIG. 33). When c-fos, c-jun and Jun B mRNA levels were assessed, an increased expression of all these genes was observed in HF-icIL-1ra fibroblasts stimulated with IL-1 that were treated with scrambled oligonucleotides (FIG. 22). These data indicated that c-fos, c-jun and Jun B were involved in icIL-1ra mediated downregulation of MMP-1 in fibroblasts.

EXAMPLE 10

Intracellular Interleukin 1receptor Antagonist Reduces the Severity of Collagen-Induced Arthritis In order to evaluate the role of one of the isoforms of interleukin 1receptor antagonist (icIL-1ra) in inducing anti-inflammatory effect, an animal model of collagen-induced arthritis was used. DBA/1-QCII24 mice transgenic for type II collagen T-cell receptor were immunized with type II collagen and seven days later were injected with an adenoviral vector containing cDNA encoding the predominant form of icIL-1ra. It was observed that these animals uniformly developed an accelerated and severe arthritis at 7-10 days following immunization with type II collagen. However, decreased severity of arthritis was observed in the injected hind paw of mice receiving icIL-1ra as compared to the mice receiving control virus containing cDNA coding for beta galactosidase (FIG. 34). At ten days post treatment, the average severity score of the icIL-1ra injected mice was 2.7 while the control mice had an average score of 4.0 (t-test, p=0.02). In addition the onset of arthritis was delayed by approximately four days in those animals receiving virus coding for icIL-1ra compared to beta-galactosidase.

The total incidence score was the same at three weeks post-immunization probably due to diminished expression of the transgene over time. Histological evaluation of the injected paw was consistent with decreased inflammation following treatment with icIL-1ra. These findings suggested that icIL-1ra lays an important role in suppressing an experimental autoimmune arthritis pathway and has potential to be pivotal player in developing new therapeutic strategies.

The following references were cited herein:

Chakraborti et al. (2003) *Mol Cell Biol* 253: 269.

Chuang-Tsai et al (2003) *Am J Pathol* 163: 445

Clark et al. (1985) *Arch. Biochem. Biophys.* 241:36-44.

Hall et al. (2003) *J Biol Chem* 278:1034

Haskill et al. (1991) *Proc. NatL. Acad. Sci. U.S.A.* 88:3681-3685.
Higgins et al. (1994) *J Exp Med* 180: 607-614.
Hugins, P. J. et al. (1999) *Exp Cell Res* 248: 634
Postlethwaite et al. (1988) *J Cell. Biol* 106:311-318.
Schmidt-Graff and Desmouliere (1994) *Virchows Archiv* 425:3.

Sugioka et al. (2004) *Int J Cancer* 109: 867.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A method of inhibiting tissue degradation, comprising
contacting a collagenase-producing cell in a tissue with an intracellular IL-1 receptor antagonist peptide(s) selected from the group consisting of SEQ ID NOs: 13, 23, and 24; and
inhibiting the expression of collagenase via said contact, thereby inhibiting tissue degradation.

2. The method of claim 1, wherein said tissue degradation is a component of chronic inflammatory disorder, wherein said chronic inflammatory disorder is arthritis, degenerative intervertebral disc disease or chronic skin ulcers.

3. A method of treating a chronic inflammatory disorder in a individual, comprising the step of administering an intracellular IL-1 receptor antagonist peptide(s) selected from the group consisting of SEQ ID NO: 13, 23, and 24 to the tissue of said individual, wherein the administration of said antagonist inhibits degradation of said tissue through inhibiting the expression of a collagenase.

4. The method of claim 3, wherein said chronic inflammatory disorder is selected from the group consisting of arthritis, degenerative intervertebral disc disease and chronic skin ulcers.

* * * * *

```
                      SEQUENCE LISTING

<160> NUMBER OF SEQ ID NOS: 41

<210> SEQ ID NO 1
<211> LENGTH: 20
<212> TYPE: DNA
<213> ORGANISM: artificial sequence
<220> FEATURE:
<223> OTHER INFORMATION: sense primer for GAPDH

<400> SEQUENCE: 1
gcagggggga gccaaaaggg                                              20

<210> SEQ ID NO 2
<211> LENGTH: 20
<212> TYPE: DNA
<213> ORGANISM: artificial sequence
<220> FEATURE:
<223> OTHER INFORMATION: antisense primer for GAPDH

<400> SEQUENCE: 2
tgccagcccc agcgtcaaag                                              20

<210> SEQ ID NO 3
<211> LENGTH: 20
<212> TYPE: DNA
<213> ORGANISM: artificial sequence
<220> FEATURE:
<223> OTHER INFORMATION: sense primer for Beta-actin

<400> SEQUENCE: 3
gtgggccgcc ccaggcacca                                              20

<210> SEQ ID NO 4
<211> LENGTH: 21
<212> TYPE: DNA
<213> ORGANISM: artificial sequence
<220> FEATURE:
<223> OTHER INFORMATION: antisense primer for Beta-actin

<400> SEQUENCE: 4
ctccttaatg tcacgcacga t                                            21

<210> SEQ ID NO 5
<211> LENGTH: 23
<212> TYPE: DNA
<213> ORGANISM: artificial sequence
<220> FEATURE:
<223> OTHER INFORMATION: sense primer for icIL-1ra type 1

<400> SEQUENCE: 5
ccaccatggc tttagagacc atc                                          23

<210> SEQ ID NO 6
<211> LENGTH: 21
<212> TYPE: DNA
<213> ORGANISM: artificial sequence
```

```
<220> FEATURE:
<223> OTHER INFORMATION: antisense primer for icIL-1ra type 1

<400> SEQUENCE: 6
ctactcgtcc tcctggaagt a                                          21

<210> SEQ ID NO 7
<211> LENGTH: 26
<212> TYPE: DNA
<213> ORGANISM: artificial sequence
<220> FEATURE:
<223> OTHER INFORMATION: sense primer for sIL-1ra

<400> SEQUENCE: 7
gaatggaaat ctgcagaggc ctccgc                                     26

<210> SEQ ID NO 8
<211> LENGTH: 19
<212> TYPE: DNA
<213> ORGANISM: artificial sequence
<220> FEATURE:
<223> OTHER INFORMATION: antisense primer for sIL-1ra

<400> SEQUENCE: 8
gtactactcg tcctcctgg                                             19

<210> SEQ ID NO 9
<211> LENGTH: 25
<212> TYPE: DNA
<213> ORGANISM: artificial sequence
<220> FEATURE:
<223> OTHER INFORMATION: sense primer for MMP-1

<400> SEQUENCE: 9
acctgaagaa tgatgggagg caagt                                      25

<210> SEQ ID NO 10
<211> LENGTH: 29
<212> TYPE: DNA
<213> ORGANISM: artificial sequence
<220> FEATURE:
<223> OTHER INFORMATION: antisense primer for MMP-1

<400> SEQUENCE: 10
catcaaaatg agcatctcct ccaatacct                                  29

<210> SEQ ID NO 11
<211> LENGTH: 23
<212> TYPE: DNA
<213> ORGANISM: artificial sequence
<220> FEATURE:
<223> OTHER INFORMATION: sense primer for TIMP-1

<400> SEQUENCE: 11
aacccaccat ggcccccttt gag                                        23

<210> SEQ ID NO 12
<211> LENGTH: 24
<212> TYPE: DNA
<213> ORGANISM: artificial sequence
<220> FEATURE:
<223> OTHER INFORMATION: antisense primer for TIMP-1

<400> SEQUENCE: 12
gttccactcc gggcaggatt cagg                                       24
```

<210> SEQ ID NO 13
<211> LENGTH: 35
<212> TYPE: PRT
<213> ORGANISM: artificial sequence
<220> FEATURE:
<223> OTHER INFORMATION: IL-1ra peptides representing the mature
      form of human sIL-1ra

<400> SEQUENCE: 13

Arg Pro Ser Gly Arg Lys Ser Ser Lys Met Gln Ala Phe Arg Ile
                 5                  10                  15

Trp Asp Val Asn Gln Lys Thr Phe Tyr Leu Arg Asn Asn Gln Leu
                20                  25                  30

Val Ala Gly Tyr Leu
                35

<210> SEQ ID NO 14
<211> LENGTH: 24
<212> TYPE: PRT
<213> ORGANISM: artificial sequence
<220> FEATURE:
<223> OTHER INFORMATION: IL-1ra peptides representing the mature
      form of human sIL-1ra

<400> SEQUENCE: 14

Gln Gly Pro Asn Val Asn Leu Glu Glu Lys Ile Asp Val Val Pro
                 5                  10                  15

Ile Glu Pro His Ala Leu Phe Leu Gly
                20

<210> SEQ ID NO 15
<211> LENGTH: 31
<212> TYPE: PRT
<213> ORGANISM: artificial sequence
<220> FEATURE:
<223> OTHER INFORMATION: IL-1ra peptides representing the mature
      form of human sIL-1ra

<400> SEQUENCE: 15

Ile His Gly Gly Lys Met Cys Leu Ser Cys Val Lys Ser Gly Asp
                 5                  10                  15

Glu Thr Arg Leu Gln Leu Glu Ala Val Asn Ile Thr Asp Leu Ser
                20                  25                  30

Glu

<210> SEQ ID NO 16
<211> LENGTH: 33
<212> TYPE: PRT
<213> ORGANISM: artificial sequence
<220> FEATURE:
<223> OTHER INFORMATION: IL-1ra peptides representing the mature
      form of human sIL-1ra

<400> SEQUENCE: 16

Asn Arg Lys Gln Asp Lys Arg Phe Ala Phe Ile Arg Ser Asp Ser
                 5                  10                  15

Gly Pro Thr Thr Ser Phe Glu Ser Ala Ala Cys Pro Gly Trp Phe
                20                  25                  30

Leu Cys Thr

<210> SEQ ID NO 17
<211> LENGTH: 29
<212> TYPE: PRT

```
<213> ORGANISM: artificial sequence
<220> FEATURE:
<223> OTHER INFORMATION: IL-1ra peptides representing the mature
      form of human sIL-1ra

<400> SEQUENCE: 17

Ala Met Glu Ala Asp Gln Pro Val Ser Leu Thr Asn Met Pro Asp
                 5                  10                  15

Glu Gly Val Met Val Thr Lys Phe Tyr Phe Gln Glu Asp Glu
                20                  25

<210> SEQ ID NO 18
<211> LENGTH: 42
<212> TYPE: PRT
<213> ORGANISM: artificial sequence
<220> FEATURE:
<223> OTHER INFORMATION: IL-1ra peptides

<400> SEQUENCE: 18

Lys Lys Lys Met Glu Lys Arg Arg Pro Ser Gly Arg Lys Ser Ser
                 5                  10                  15

Lys Met Gln Ala Phe Arg Ile Trp Asp Val Asn Gln Lys Thr Phe
                20                  25                  30

Tyr Leu Arg Asn Asn Gln Leu Val Ala Gly Tyr Leu
                35                  40

<210> SEQ ID NO 19
<211> LENGTH: 15
<212> TYPE: PRT
<213> ORGANISM: artificial sequence
<220> FEATURE:
<223> OTHER INFORMATION: IL-1ra peptides

<400> SEQUENCE: 19

Arg Pro Ser Gly Arg Lys Ser Ser Lys Met Gln Ala Phe Arg Ile
                 5                  10                  15

<210> SEQ ID NO 20
<211> LENGTH: 17
<212> TYPE: PRT
<213> ORGANISM: artificial sequence
<220> FEATURE:
<223> OTHER INFORMATION: IL-1ra peptides

<400> SEQUENCE: 20

Met Gln Ala Phe Arg Ile Trp Asp Val Asn Gln Lys Thr Phe Tyr
                 5                  10                  15

Leu Phe

<210> SEQ ID NO 21
<211> LENGTH: 15
<212> TYPE: PRT
<213> ORGANISM: artificial sequence
<220> FEATURE:
<223> OTHER INFORMATION: IL-1ra peptides

<400> SEQUENCE: 21

Phe Tyr Leu Arg Asn Asn Gln Leu Val Ala Gly Tyr Leu Gln Gly
                 5                  10                  15

<210> SEQ ID NO 22
<211> LENGTH: 7
<212> TYPE: PRT
<213> ORGANISM: artificial sequence
<220> FEATURE:
```

<223> OTHER INFORMATION: IL-1ra peptides

<400> SEQUENCE: 22

Phe Tyr Leu Arg Asn Asn Gln
              5

<210> SEQ ID NO 23
<211> LENGTH: 8
<212> TYPE: PRT
<213> ORGANISM: artificial sequence
<220> FEATURE:
<223> OTHER INFORMATION: IL-1ra peptides

<400> SEQUENCE: 23

Asn Asn Gln Leu Val Ala Gly Tyr
              5

<210> SEQ ID NO 24
<211> LENGTH: 8
<212> TYPE: PRT
<213> ORGANISM: artificial sequence
<220> FEATURE:
<223> OTHER INFORMATION: IL-1ra peptides

<400> SEQUENCE: 24

Leu Val Ala Gly Tyr Leu Gln Gly
              5

<210> SEQ ID NO 25
<211> LENGTH: 23
<212> TYPE: DNA
<213> ORGANISM: artificial sequence
<220> FEATURE:
<223> OTHER INFORMATION: MMP-1 forward primer

<400> SEQUENCE: 25
ggcttgaagc tgcttacgaa ttt                                              23

<210> SEQ ID NO 26
<211> LENGTH: 24
<212> TYPE: DNA
<213> ORGANISM: artificial sequence
<220> FEATURE:
<223> OTHER INFORMATION: MMP-1 reverse primer

<400> SEQUENCE: 26
gaagccaaag gagctgtaga tgtc                                             24

<210> SEQ ID NO 27
<211> LENGTH: 29
<212> TYPE: DNA
<213> ORGANISM: artificial sequence
<220> FEATURE:
<223> OTHER INFORMATION: MMP-1 specific probe

<400> SEQUENCE: 27
tccctttgaa aaccggact tcatctctg                                         29

<210> SEQ ID NO 28
<211> LENGTH: 18
<212> TYPE: DNA
<213> ORGANISM: artificial sequence
<220> FEATURE:
<223> OTHER INFORMATION: GAPDH forward primer

<400> SEQUENCE: 28
gaaggtgaag gtcggagt                                                 18

<210> SEQ ID NO 29
<211> LENGTH: 20
<212> TYPE: DNA
<213> ORGANISM: artificial sequence
<220> FEATURE:
<223> OTHER INFORMATION: GAPDH reverse primer

<400> SEQUENCE: 29
gaaatcccat caccatcttc                                               20

<210> SEQ ID NO 30
<211> LENGTH: 20
<212> TYPE: DNA
<213> ORGANISM: artificial sequence
<220> FEATURE:
<223> OTHER INFORMATION: JOE-labeled probe

<400> SEQUENCE: 30
ccgactcttg cccttcgaac                                               20

<210> SEQ ID NO 31
<211> LENGTH: 21
<212> TYPE: DNA
<213> ORGANISM: artificial sequence
<220> FEATURE:
<223> OTHER INFORMATION: sense alpha-SMA primer

<400> SEQUENCE: 31
gtccccatct atgagggcta t                                             21

<210> SEQ ID NO 32
<211> LENGTH: 21
<212> TYPE: DNA
<213> ORGANISM: artificial sequence
<220> FEATURE:
<223> OTHER INFORMATION: antisene alpha-SMA primer

<400> SEQUENCE: 32
gcatttgcgg tggacaatgg a                                             21

<210> SEQ ID NO 33
<211> LENGTH: 24
<212> TYPE: DNA
<213> ORGANISM: artificial sequence
<220> FEATURE:
<223> OTHER INFORMATION: sense PAI primer

<400> SEQUENCE: 33
aaggaccgca acgtggtttt ctca                                          24

<210> SEQ ID NO 34
<211> LENGTH: 22
<212> TYPE: DNA
<213> ORGANISM: artificial sequence
<220> FEATURE:
<223> OTHER INFORMATION: antisense PAI primer

<400> SEQUENCE: 34
tgaagaagtg gggcatgaag cc                                            22

<210> SEQ ID NO 35
<211> LENGTH: 22
<212> TYPE: DNA
<213> ORGANISM: artificial sequence

```
<220> FEATURE:
<223> OTHER INFORMATION: sense c-fos primer

<400> SEQUENCE: 35
agctgcacta cctatacgtc tt                                              22

<210> SEQ ID NO 36
<211> LENGTH: 21
<212> TYPE: DNA
<213> ORGANISM: artificial sequence
<220> FEATURE:
<223> OTHER INFORMATION: antisense c-fos primer

<400> SEQUENCE: 36
tcaagtcctt gaggtccaca g                                               21

<210> SEQ ID NO 37
<211> LENGTH: 21
<212> TYPE: DNA
<213> ORGANISM: artificial sequence
<220> FEATURE:
<223> OTHER INFORMATION: sense c-jun primer

<400> SEQUENCE: 37
gtcatgaacc acgttaacgt g                                               21

<210> SEQ ID NO 38
<211> LENGTH: 21
<212> TYPE: DNA
<213> ORGANISM: artificial sequence
<220> FEATURE:
<223> OTHER INFORMATION: antisense c-jun primer

<400> SEQUENCE: 38
tccatgcagt tcttgtcaat g                                               21

<210> SEQ ID NO 39
<211> LENGTH: 21
<212> TYPE: DNA
<213> ORGANISM: artificial sequence
<220> FEATURE:
<223> OTHER INFORMATION: sense Jun B primer

<400> SEQUENCE: 39
agctcaagca gaaggtcatg a                                               21

<210> SEQ ID NO 40
<211> LENGTH: 21
<212> TYPE: DNA
<213> ORGANISM: artificial sequence
<220> FEATURE:
<223> OTHER INFORMATION: antisense Jun B primer

<400> SEQUENCE: 40
atgtaaacct cgaggtggaa g                                               21

<210> SEQ ID NO 41
<211> LENGTH: 18
<212> TYPE: DNA
<213> ORGANISM: artificial sequence
<220> FEATURE:
<223> OTHER INFORMATION: icIL-1ra type 1

<400> SEQUENCE: 41
cgtctgtaaa ggcatggg                                                   18
```